United States Patent
Chang et al.

(10) Patent No.: US 7,255,833 B2
(45) Date of Patent: Aug. 14, 2007

(54) APPARATUS AND REACTION VESSEL FOR CONTROLLING THE TEMPERATURE OF A SAMPLE

(75) Inventors: Ronald Chang, Redwood City, CA (US); Lee A. Christel, Palo Alto, CA (US); Gregory T. A. Kovacs, Stanford, CA (US); William A. McMillan, Cupertino, CA (US); M. Allen Northrup, Berkeley, CA (US); Kurt E. Petersen, Santa Clara, CA (US); Farzad Pourahmadi, Fremont, CA (US); Steven J. Young, Los Gatos, CA (US); Robert Yuan, Belmont, CA (US); Douglas B. Dority, Mill Valley, CA (US)

(73) Assignee: Cepheid, Sunnyvale, CA (US)

( * ) Notice: Subject to any disclaimer, the term of this patent is extended or adjusted under 35 U.S.C. 154(b) by 692 days.

(21) Appl. No.: 10/379,291

(22) Filed: Mar. 3, 2003

(65) Prior Publication Data
US 2003/0152492 A1    Aug. 14, 2003

Related U.S. Application Data

(62) Division of application No. 09/194,374, filed on Jul. 25, 2000, now Pat. No. 6,565,815.

(51) Int. Cl.
*G01N 21/00* (2006.01)

(52) U.S. Cl. .......................... 422/58; 422/100; 422/102; 422/68.1; 422/82.05

(58) Field of Classification Search ................. 422/58, 422/100, 82.05, 82.12, 68.1, 102, 104
See application file for complete search history.

(56) References Cited

U.S. PATENT DOCUMENTS

| | | | |
|---|---|---|---|
| 3,708,886 | A | 1/1973 | Ogle |
| 3,937,614 | A | 2/1976 | Sodickson et al. |
| 4,192,429 | A | 3/1980 | Yerman |
| 4,207,394 | A | 6/1980 | Aldridge, Jr. et al. |
| 4,301,117 | A | 11/1981 | Smernoff |
| 4,396,579 | A | 8/1983 | Schroeder et al. |
| 4,810,653 | A | 3/1989 | Helfer et al. |

(Continued)

FOREIGN PATENT DOCUMENTS

EP    0 318 255    5/1989

(Continued)

OTHER PUBLICATIONS

Wittwer, et al., "The LightCycler. TM.: A Microvolume Multisample Fluorimeter with Rapid Temperature Control" BioTechniques 22: 176-181 (Jan. 1997).

*Primary Examiner*—Brian R. Gordon
(74) *Attorney, Agent, or Firm*—Townsend and Townsend and Crew, LLP

(57) ABSTRACT

This invention provides an apparatus for rapidly heating and/or cooling a sample in a reaction vessel. In some embodiments, the apparatus includes optics for the efficient detection of a reaction product in the vessel. The invention also provides a reaction vessel having a reaction chamber designed for optimal thermal conductance and for efficient optical viewing of reaction products in the chamber.

74 Claims, 11 Drawing Sheets

U.S. PATENT DOCUMENTS

| | | |
|---|---|---|
| 4,902,624 A | 2/1990 | Columbus et al. |
| 4,933,146 A | 6/1990 | Meyer et al. |
| 5,026,526 A | 6/1991 | Quenin et al. |
| 5,038,852 A | 8/1991 | Johnson et al. |
| 5,077,017 A | 12/1991 | Gorin et al. |
| 5,104,813 A | 4/1992 | Besemer et al. |
| 5,333,675 A | 8/1994 | Mullis et al. |
| 5,343,909 A | 9/1994 | Goodman |
| 5,376,313 A | 12/1994 | Kanewske, III et al. |
| 5,460,780 A | 10/1995 | Devaney, Jr. et al. |
| 5,589,136 A | 12/1996 | Northrup et al. |
| 5,652,149 A | 7/1997 | Mileaf et al. |
| 5,656,493 A | 8/1997 | Mullis et al. |
| 5,709,840 A | 1/1998 | Juranas |
| 5,711,917 A | 1/1998 | Juranas et al. |
| 5,721,136 A | 2/1998 | Finney et al. |
| 5,783,148 A | 7/1998 | Cottingham et al. |
| 5,786,182 A | 7/1998 | Catanzariti et al. |
| 5,811,296 A | 9/1998 | Chemelli et al. |
| 5,928,907 A | 7/1999 | Woudenberg et al. |
| 5,958,349 A * | 9/1999 | Petersen et al. ............ 422/198 |
| 6,144,448 A | 11/2000 | Mitoma |
| 6,184,029 B1 | 2/2001 | Wilding et al. |
| 6,369,893 B1 | 4/2002 | Christel et al. |
| 6,391,541 B1 | 5/2002 | Petersen et al. |
| 6,403,037 B1 * | 6/2002 | Chang et al. ............... 422/68.1 |
| 6,431,476 B1 | 8/2002 | Taylor et al. |
| 6,489,111 B1 | 12/2002 | Takahashi et al. |
| 6,565,815 B1 | 5/2003 | Yuan et al. |
| 6,660,228 B1 * | 12/2003 | Chang et al. ............... 422/68.1 |
| 6,818,185 B1 * | 11/2004 | Petersen et al. ............ 422/102 |
| 7,101,509 B2 | 9/2006 | Chang et al. |
| 2002/0168299 A1 * | 11/2002 | Chang et al. ................ 422/102 |
| 2005/0042137 A1 * | 2/2005 | Petersen et al. ............... 422/58 |
| 2005/0112023 A1 | 5/2005 | Liang |

FOREIGN PATENT DOCUMENTS

| | | |
|---|---|---|
| EP | 0 436 995 | 7/1991 |
| EP | 0 545 736 | 6/1993 |
| EP | 0 603 411 | 6/1994 |
| EP | 0 606 961 | 7/1994 |
| EP | 0 662 345 | 7/1995 |
| EP | 1 045 038 | 10/2000 |
| JP | 0 693 560 | 1/1996 |

* cited by examiner

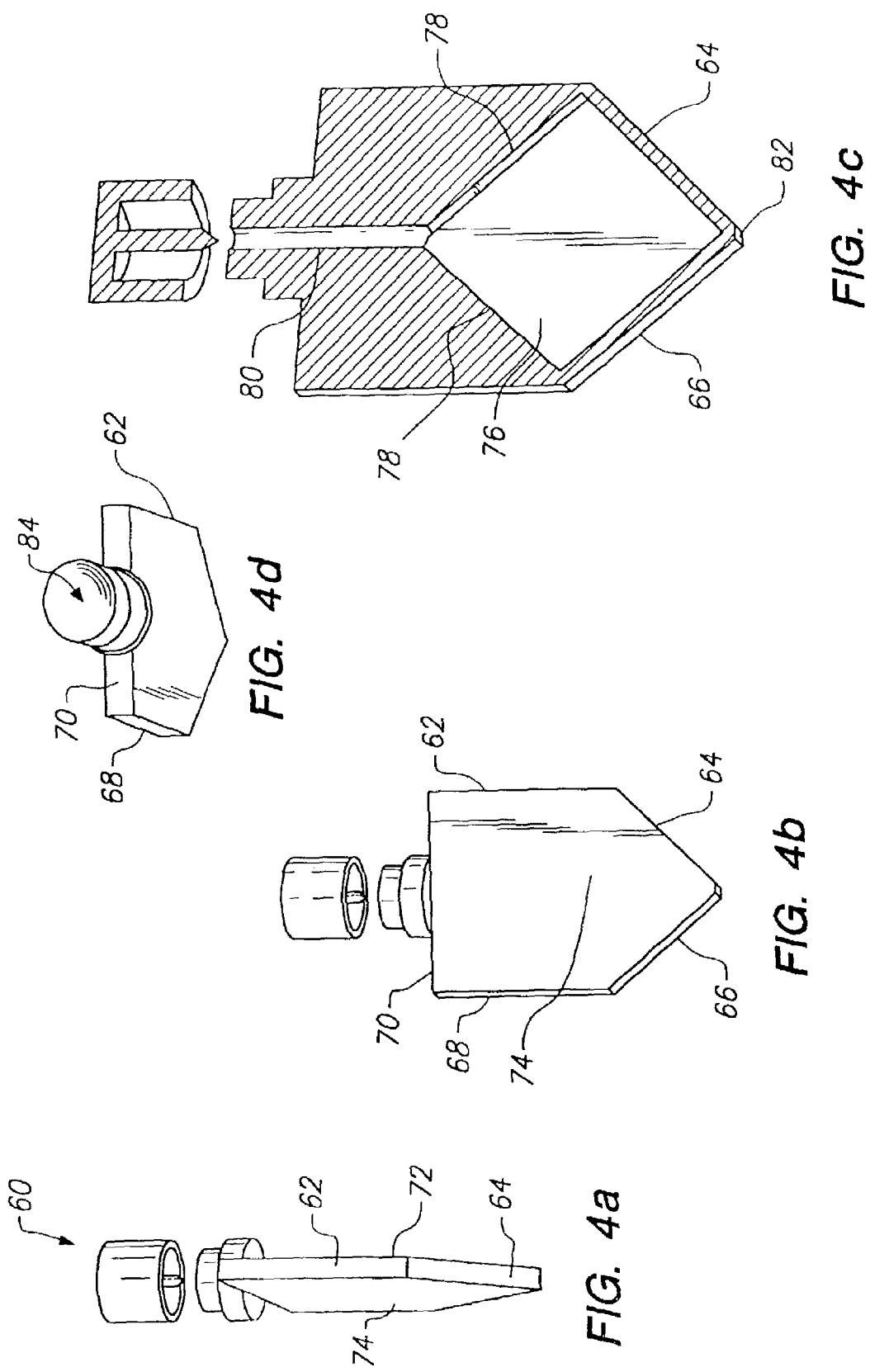

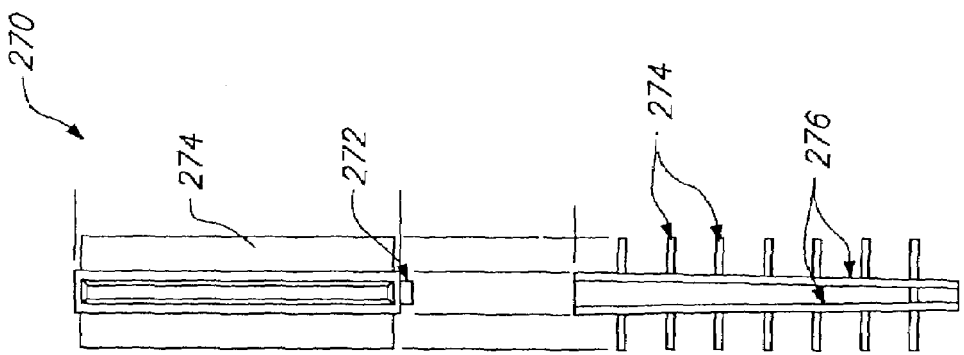
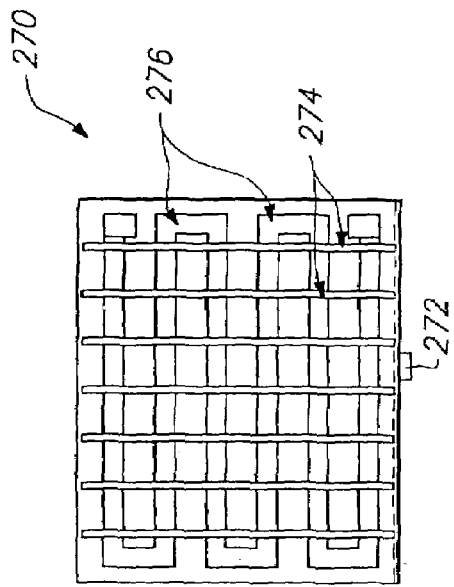
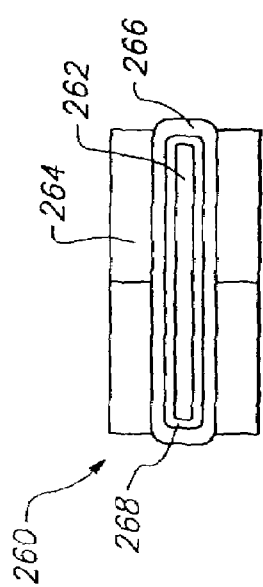
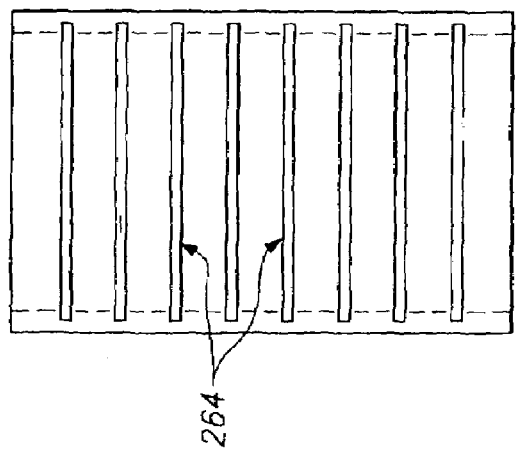
FIG. 8d
FIG. 8c
FIG. 8a
FIG. 8b

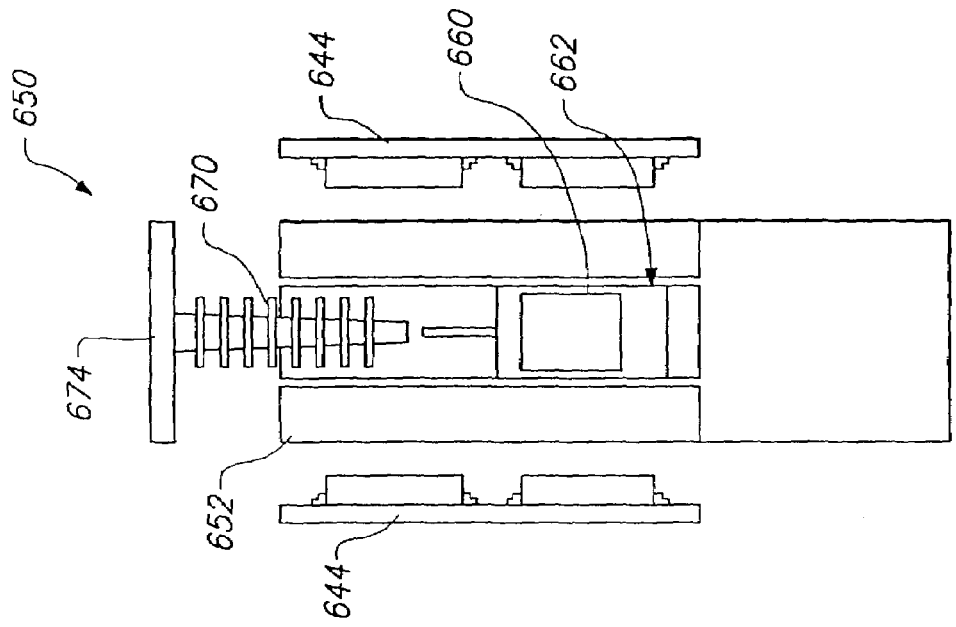
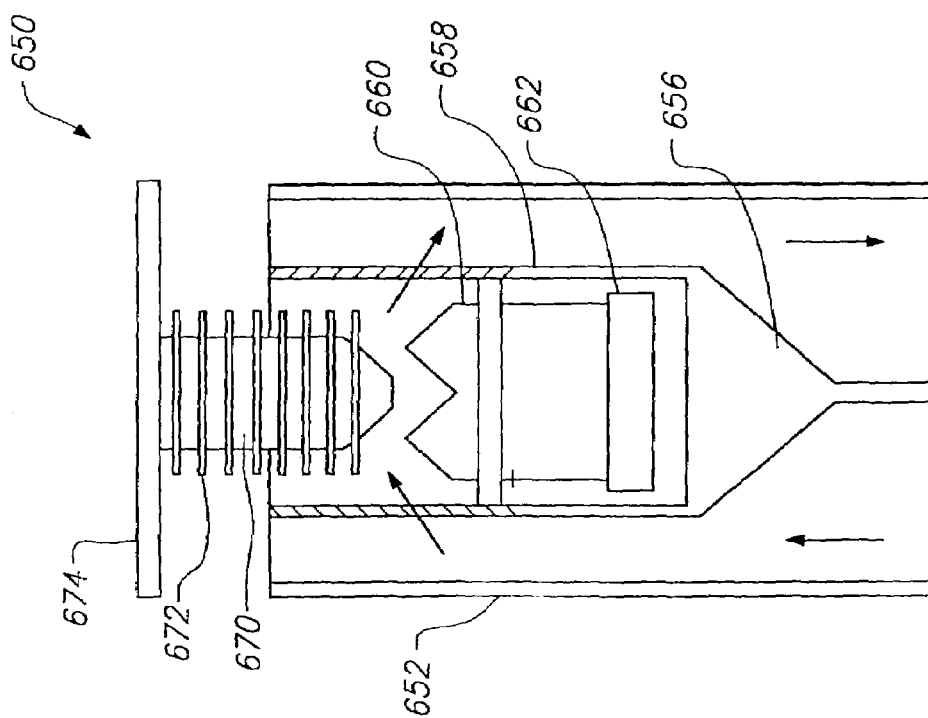

APPARATUS AND REACTION VESSEL FOR CONTROLLING THE TEMPERATURE OF A SAMPLE

CONTINUING APPLICATION DATA

This application is a division of U.S. Ser. No. 09/194,374, which is the National Stage of International Application No. PCT/US98/03962, filed Mar. 2, 1998, which international application claims priority from U.S. Ser. No. 08/808,325, filed Feb. 28, 1997, now U.S. Pat. No. 5,958,349, U.S. Ser. No. 08/808,327, filed Feb. 28, 1997, now abandoned, and U.S. Ser. No. 08/808,733, filed Feb. 28, 1997, now abandoned. All of these applications are incorporated herein by reference for all purposes.

This invention was made with Government support under contract DAAM01-96-C-0061 awarded by the U.S. Army. The Government has certain rights in the invention.

FIELD OF THE INVENTION

The present invention provides an apparatus and reaction vessel for controlling the temperature of a sample.

BACKGROUND OF THE INVENTION

There are many applications in the field of chemical processing in which it is desirable to precisely control the temperature of chemicals and to induce rapid temperature transitions. In these reactions, heat is exchanged between chemicals and their environment to increase or decrease the temperature of the reacting chemicals. It is often desirable to control the temperature change in a manner that accurately attains the target temperature, avoids undershooting or overshooting of the temperature, and quickly reaches the target temperature. Such control of temperature may inhibit side reactions, the formation of unwanted bubbles, the degradation of components at certain temperatures, etc., which may occur at non-optimal temperatures. It is of further interest to optically observe and monitor the chemical reaction.

Applications for heat exchanging chemical reactions may encompass organic, inorganic, biochemical and molecular reactions, and the like. In organic and inorganic reactions, chemicals may be heated to achieve the activation energy for the reaction. Examples of thermal chemical reactions include isothermal nucleic acid amplification, thermal cycling amplification, such as polymerase chain reaction (PCR), ligase chain reaction (LCR), self-sustained sequence replication, enzyme kinetic studies, homogenous ligand binding assays, and more complex biochemical mechanistic studies that require complex temperature changes. Temperature control systems also enable the study of certain physiologic processes where a constant and accurate temperature is required.

Numerous devices and systems have been described in the art for conducting thermal transfer reactions. These devices use a variety of designs for heat transfer, such as water baths, air baths, and solid blocks such as aluminum. Chemical reactions in small reaction volumes have also been described.

Conventional instrumentation, for example, typically consists of a block of aluminum having as many as ninety-six conical reaction tubes. The aluminum block is heated and cooled either by a Peltier heating/cooling apparatus, or by a closed-loop liquid heating/cooling system, flowing through channels machined into the aluminum block. Because of the large thermal mass of the aluminum block, heating and cooling rates are limited to about 1° C./sec resulting in longer processing times. For example, in the PCR application, fifty cycles may require two or more hours to complete.

Part of the reason for the relatively large metal block is to provide sufficient mass to ensure a constant and uniform temperature at each reaction site, as well as from site to site. Some chemical reaction instruments also incorporate a top-plate, which is heated and cooled to ensure a uniform temperature across the top of all sample solutions. The sample inserts are tapered to maximize thermal contact between the insert and the metal block. One problem with these instruments is that the large thermal masses, required for temperature uniformity, take a long time (and or a large heating/cooling power source) to heat and to cool. Usual heating and cooling rates for these types of instruments are on the order of 1-3° C./second.

Typically, the highest heating rate obtainable in commercial instruments is on the order of 3° C./second, and cooling rates are significantly less. With these relatively slow heating and cooling rates, it has been observed that some processes requiring high control of temperature are inefficient. For example, reactions may occur at the intermediate temperatures, creating unwanted and interfering side products, such as in PCR "primerdimers" or anomalous amplicons, which are deleterious to the analytical process. The poor control of temperature also results in over consumption of reagents necessary for the intended reaction.

Furthermore, for some diagnostic and environmental chemical detection methodologies, the volume of the tested unknown sample can be important. For example, in the detection of viruses in blood or other bodily fluids using PCR, the detection limit is about 10 virions. Therefore, a minimum fluid volume is required depending upon the concentration of virions in the sample. By way of illustration, at a concentration of 100 virions/mL, the sample size should be at least 0.1 mL. For more dilute samples, even larger sample volumes are necessary. Therefore, the chemical analysis system should be capable of handling milliliter fluid volumes.

Another requirement in many chemical analyses is the ability to monitor the chemical reaction and detect the resulting product. A preferred detection technique is optical interrogation, typically using fluorescence or chemiluminescence. For ligand-binding assays, time-resolved fluorescence and fluorescence polarization are often used.

The control of heating and cooling changes may be referred to as thermal cycling. The term "thermal cycling" is herein intended to mean at least one change of temperature, i.e. increase or decrease of temperature, in the environment to which chemicals are exposed. Therefore, chemicals undergoing thermal cycling may shift from one temperature to another and then stabilize at that temperature, transition to a second temperature or return to the starting temperature. The temperature cycle may be performed once or repeated as many times as required by the particular chemical reaction. The various chemical reactions occurring during these temperature cycles are more specific and more efficient when the temperature is raised and lowered to the various required reaction temperatures as quickly as possible and controlled very precisely.

Devices which control the transfer of heat for chemical reactions are applicable for synthesis reactions such as thermal cycling PCR to amplify a segment of nucleic acid. In this methodology, a DNA template is used with a thermostable DNA polymerase, eg., Taq DNA polymerase, nucleoside triphosphates, and two oligonucleotides with different sequences, complementary to sequences that lie on opposite strands of the template DNA and which flank the segment of DNA that is to be amplified ("primers"). The reaction components are cycled between a higher temperature (e.g., 95° C.) for dehybridizing double stranded template DNA, followed by lower temperatures (e.g., 40-60° C. for annealing of primers and 70-75° C. for polymerization). Repeated cycling among dehybridization, annealing, and polymerization temperatures provides exponential amplification of the template DNA. For example, up to 1 µg of target DNA up to 2 kb in length can be obtained with 30-35 cycles of amplification from only $10^{-6}$ µg of starting DNA.

Polynucleotide amplification has been applied to the diagnosis of genetic disorders; the detection of nucleic acid sequences of pathogenic organisms in a variety of samples including blood, tissue, environmental, air borne, and the like; the genetic identification of a variety of samples including forensic, agricultural, veterinarian, and the like; the analysis of mutations in activated oncogenes, detection of contaminants in samples such as food; and in many other aspects of molecular biology. Polynucleotide amplification assays can be used in a wide range of applications such as the generation of specific sequences of cloned double-stranded DNA for use as probes, the generation of probes specific for uncloned genes by selective amplification of particular segments of cDNA, the generation of libraries of cDNA from small amounts of mRNA, the generation of large amounts of DNA for sequencing and the analysis of mutations. Instruments for performing automated PCR chain reactions via thermal cycling are commercially available.

Some of the instrumentation suitable for newer processes, requiring "real-time" optical analysis after each thermal cycle, has only recently become available. For example, the Perkin Elmer (PE) 7700 (ATC) instrument as well as the PE 9600 thermal cycler are based on a 96-well aluminum block format, as described above. Optical fluorescence detection in the PE 7700 is accomplished by guiding an optical fiber to each of the ninety-six reaction sites. A central high power laser sequentially excites each reaction tube and captures the fluorescence signal through the optical fiber. Complex beam-guiding and optical multiplexing are typically required.

A different thermal cycling instrument is available from Idaho Technologies. This instrument employs forced-air heating and cooling of capillary sample carriers mounted in a carousel. The instrument monitors each capillary sample carrier in sequence as the capillary sample carriers are rotated past an optical detection site.

A third real-time PCR analysis system is the MATCI device developed by Dr. Allen Northrup et al., as disclosed in U.S. Pat. No. 5,589,136, incorporated herein by reference. This device uses a modular approach to PCR thermal cycling and optical analysis. Each reaction is performed in its own silicon sleeve and each sleeve has its own associated optical excitation source and fluorescence detector. The low thermal mass of the thermal cycling sleeve allows the MATCI device to realize fast thermal heating and cooling rates, up to 30° C./sec heating and 5° C./sec cooling.

There are, however, disadvantages to this MATCI device in its use of a micromachined silicon sleeve that incorporates a heating element directly deposited on the sleeve. A first disadvantage is that the brittle silicon sleeve may crack and chip. A second disadvantage is that it is difficult to micromachine a silicon sleeve and heating element with sufficient precision to allow the sleeve to precisely accept a plastic insert that holds the sample.

For the reasons stated above, optimization of many biochemical reaction processes, including the PCR process, require that the desired reaction temperatures be reached as quickly as possible, spending minimal time at intermediate temperatures. Therefore, the heating and cooling system in which the sample reacts should permit rapid heating and cooling rates. It is also desirable that such a system permit real time optical interrogation of the sample.

SUMMARY

A reaction vessel and apparatus for performing heat-exchanged chemical reactions are provided. The reaction vessel and apparatus are designed for optimal thermal transfer to or from a sample and for efficient optical viewing of a chemical reaction with the sample.

In accordance with an aspect of the present invention, an apparatus for controlling the temperature of a sample comprises a vessel having a chamber defined by two opposing major walls and a plurality of rigid minor walls joining the major walls to each other. At least one of the major walls comprises a sheet or film. The vessel also includes a port for introducing fluid into the chamber, and a channel connecting the port to the chamber. The apparatus also includes at least one heating surface for contacting the sheet or film, the sheet or film being sufficiently flexible to conform to the surface. The apparatus further includes a plug that is insertable into the channel to increase pressure in the chamber, whereby the pressure increase in the chamber forces the sheet or film against the heating surface.

Another aspect of the present invention is directed to a vessel having a reaction chamber for holding a sample. The vessel comprises a rigid frame defining the minor walls of the chamber. At least two of the minor walls are light transmissive to provide optical windows to the chamber. At least one sheet or film is attached to the rigid frame to form a major wall of the chamber. The vessel also includes a port for introducing the sample into the chamber.

In some embodiments, the vessel includes at least two sheets or films that are attached to opposite sides of the frame to form two opposing major walls of the chamber, each of the sheets or films being sufficiently flexible to conform to a respective heating surface. In some embodiments, the light transmissive walls are angularly offset from each other, preferably by about 90°.

Another aspect of the present invention is directed to a vessel having a reaction chamber for holding a sample. The vessel comprises a rigid frame defining the minor walls of the chamber. At least one sheet or film is attached to the rigid frame to form a major wall of the chamber. The vessel also comprises a port for introducing the sample into the vessel; a channel connecting the port to the chamber; and a plug that is insertable into the channel to increase pressure in the chamber. In some embodiments, the vessel includes at least two sheets or films that are attached to opposite sides of the frame to form two opposing major walls of the chamber, each of the sheets or films being sufficiently flexible to conform to a respective heating surface.

Another aspect of the present invention is directed to a vessel comprising two opposing major walls and a plurality of rigid minor walls joining the major walls to each other to form a reaction chamber. At least one of the major walls comprises a sheet or film, and at least two of the minor walls are light transmissive. The vessel includes a port for introducing fluid into the chamber. In some embodiments, the ratio of the total surface area of the major walls to that of the minor walls is at least 2:1. In some embodiments, the ratio of the thermal conductance of the major walls to that of the minor walls is at least 2:1.

BRIEF DESCRIPTION OF THE DRAWINGS

FIG. 2a shows the module prior to biasing the sleeve against the vessel.

FIGS. 4a, b, c, d show various views of another embodiment of a reaction vessel according to the present invention. FIG. 4a shows a side view of the vessel, FIG. 4b shows a front view of the vessel, FIG. 4c shows a cross sectional view of the vessel with a channel leading to a reaction chamber, and FIG. 4d shows a top view of the vessel.

FIGS. 8a, b, c, d show various heating and cooling configurations of a thermal sleeve according to alternative embodiments of the present invention. FIG. 8a is a top view of the heating and cooling elements of a sleeve, FIG. 8b is a front view of the cooling elements shown in FIG. 8a, FIG. 8c is a front view of another sleeve with heating and cooling elements, and FIG. 8d is a side view of the sleeve shown in FIG. 8c.

FIGS. 10a, b show schematic views of a heat exchanging unit according to another embodiment of the invention. FIG. 10a shows a front view of the unit, and FIG. 10b shows a side view of the unit.

FIG. 11a shows four units interfacing with a main controller board of the base support.

DETAILED DESCRIPTION

In general, this invention provides a low thermal mass heating and cooling assembly for the rapid heating and cooling of chemical solutions to perform reactions and for the efficient detection of the reaction products. The low thermal mass of the system ensures rapid heating and cooling rates since there is little material to heat and cool and because there is a high surface to volume ratio for thermal transfer. Those skilled in the art have only recently appreciated that rapid heating and cooling improves efficiency and decreases the amount of extraneous undesirable reactions, and that certain reactions could be performed with high thermal exchange rates.

The objectives of the invention are to greatly increase thermal exchange rates in chemical processes, such as PCR (up to 10× faster heating and cooling rates), to optimize temperature uniformity of the reactants, to accommodate high thermal expansion coefficients to minimize thermal-induced mechanical stress; maximize optical excitation efficiency (long optical pathlength), to maximize optical detection sensitivity (maximize photon collection volume), to maximize fault detection capability, to minimize computer overhead of the host instrument, and to minimize overall power consumption of the instrument via independent, modular, intelligent reaction units supported by a powerful instrument platform and technology for long term versatility.

The objectives of the invention are attained via self-contained heat-exchanging units with optics. Each modular, heat-exchanging unit constitutes a single reaction site. Overall, each unit comprises (a) a thermal sleeve for receiving a reaction vessel, wherein the thermal sleeve has integral heating element(s) for heating a reaction mixture contained in the vessel; (b) a pair of optics assemblies that incorporate solid-state excitation and detection sources; (c) a cooling system, e.g., a fan or Peltier device, for cooling the reaction mixture; and (d) a housing for the thermal sleeve, optics assemblies, and cooling system.

The modular, heat exchanging unit(s) may be supported by a base support having one or multiple circuit boards with microcontrollers for monitoring control of the light excitation and detection sources and for communicating with a host computer. The base support may include a main controller board which communicates with the optics assemblies, thermal sleeve, and reaction chamber to control procedures such as temperature and optical control; self-diagnostic protocols; and receipt, storage and processing of data, wherein each heat exchanging unit may be separately controlled or the cluster of units may be under a single set of controls.

Reaction Vessel

Figure 1:
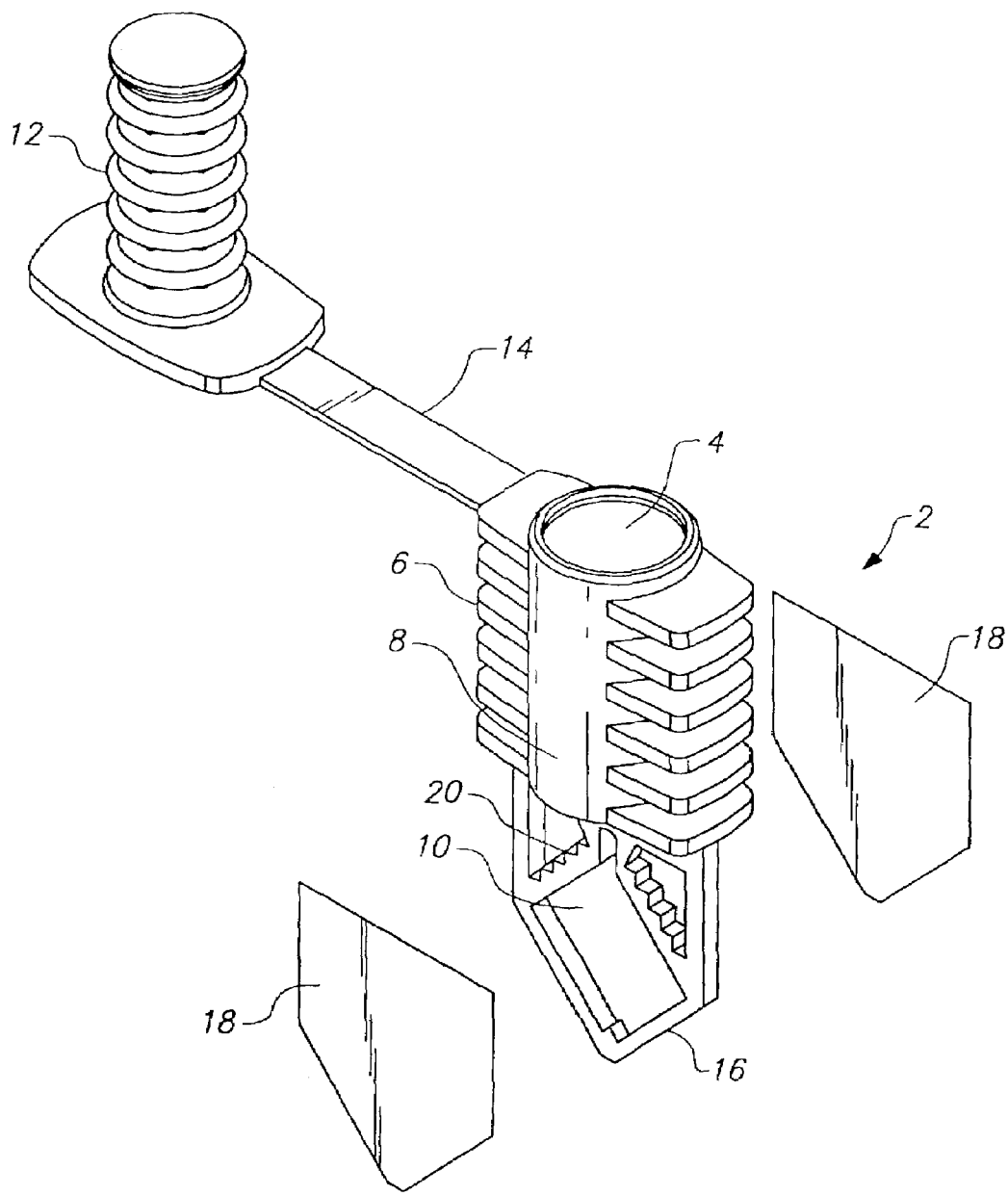
FIG. 1 shows a partially exploded, isometric view of a reaction vessel having a reaction chamber, wherein two walls of the reaction chamber are removed to show the interior of the chamber.

FIG. 1 shows a partially exploded view of a reaction vessel according to the present invention. The vessel includes a reaction chamber for holding a sample for chemical reaction. The vessel is designed for optimal thermal conductance and for efficient optical viewing of the reaction product. The thin shape of the vessel contributes to optimal thermal kinetics by providing large surfaces for thermal conduction and for contacting temperature-regulating elements, e.g., thermal plates. In addition, the minor or major walls provide windows into the chamber so that the entire reaction mix can be optically interrogated. In addition, the vessel is suitable for a wide range of reaction volumes.

In more detail to the components shown in FIG. 1, a reaction vessel (2) has a housing (6) defining a port (4) and a channel (8) connecting the port (4) to a reaction chamber (10). A seal cap (12) for sealing the port (4) is attached to the housing (6) by a flexible arm (14). The cap (12) is insertable into the port (4) to engage channel (8). A rigid support frame (16) and thin flexible walls (18), shown in FIG. 1 exploded from the frame, define the chamber (10), wherein the flexible walls (18) are coupled to opposite sides of the frame (16). On the rigid frame (16) are reflective faces (20) which bounce back light transmitted from the chamber (10), allowing for increased detection of signal.

In using the reaction vessel (2), a sample added to port (4) flows through the channel (8) and into chamber (10). In the chamber (10) the sample is introduced to chemicals for reacting. The major walls (18) of the chamber (10) are made to press against heating or cooling elements, e.g., thermal plates, and the walls (18) conform to the element surface. The sample is exposed to variations in temperature by activating the heating/cooling element. The reaction and/or reaction products are optically viewed.

The thin, flexible walls (18) which define the sides of the chamber (10) facilitate optimal thermal conductance to the chemicals contained in the chamber (10). The flexible nature of the walls (18) allow for maximum contact with a heating or cooling source. The walls are conformable to the surface of an external thermal element such that the surface of the flexible walls may adapt to the shape of the external heating/cooling element surface in a manner that avoids or minimizes gaps between the two surfaces. Furthermore, the flexible wall continues to conform to the thermal surface if the surface shape changes during the course of the heat exchanging operation. For example, as the heating element expands due to the increased temperature, the chamber wall also expands to maintain optimal contact with the heating element. Also, if the walls expand due to an increase of internal pressure within the chamber, the walls do not become rigid, but remain conformed to the heating or cooling surface. Contact may be made by biasing the thermal source against the walls and/or by pressing the walls against the thermal surface.

Figure 2B:
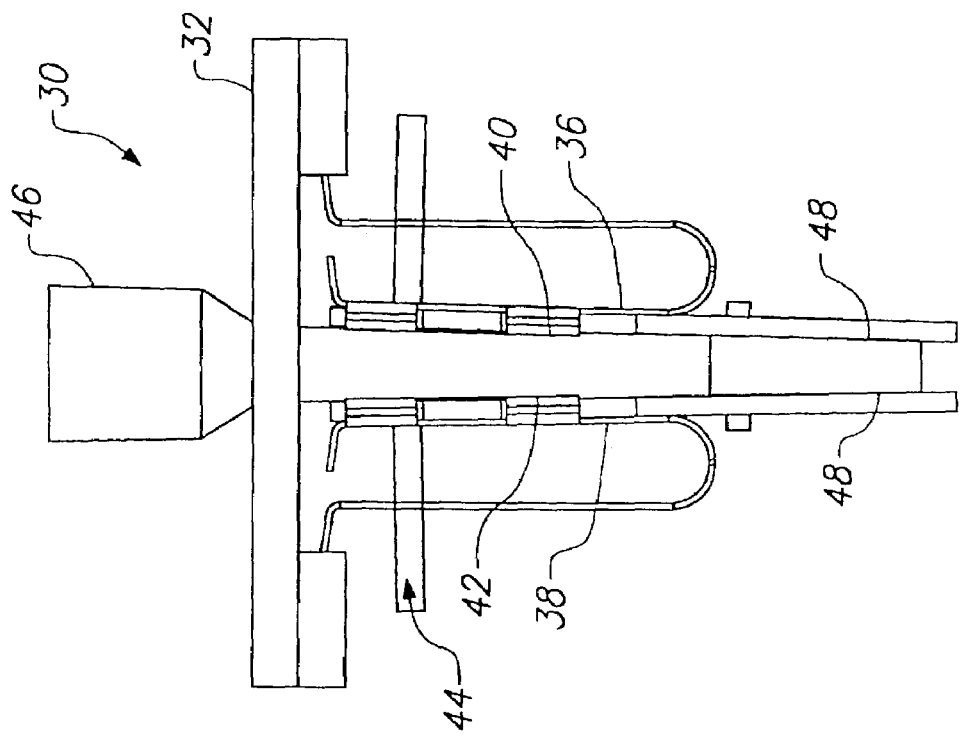
FIG. 2b shows the module after the sleeve is made to bias against the inserted vessel.
Figure 2A:
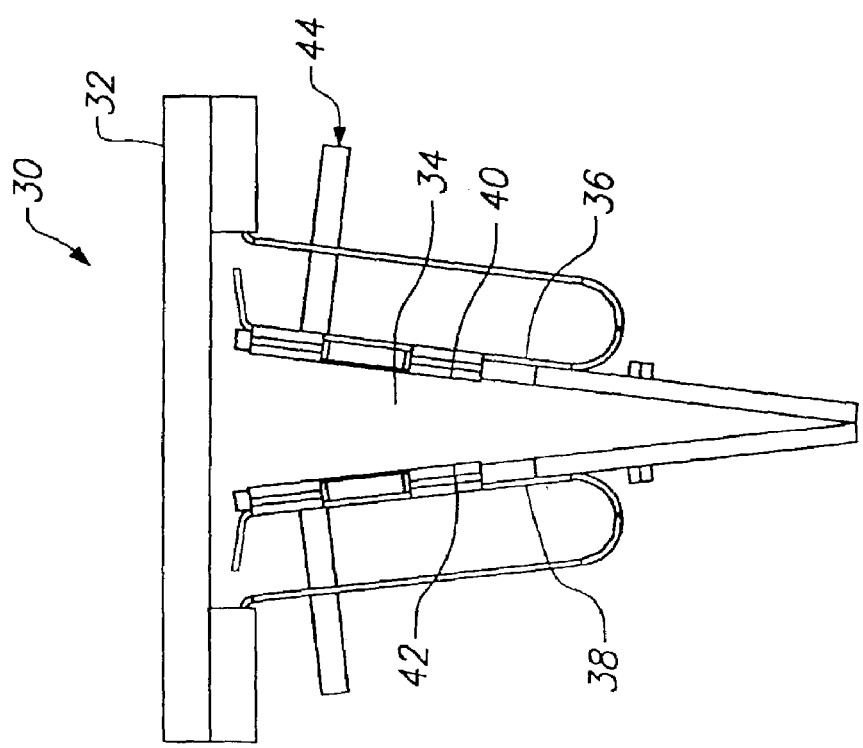
FIGS. 2a, b show schematic, side views of a heat-exchanging module with a reaction vessel and thermal sleeve.

FIGS. 2a and 2b demonstrate the contact a reaction vessel (46) makes with a thermal sleeve (32) to form a heat exchanging module (30). In FIG. 2a, the thermal sleeve (32) includes thermal plates (36), (38) which are in a relaxed position with opening (34) between the plates. However, as depicted in FIG. 2b, when the reaction vessel (46) with flexible walls (48) is inserted in the opening between the plates (36), (38), the plate surfaces (40), (42) fully engage the chamber walls (48). In this activated position, minimal or no gaps are found between the plate surfaces and the chamber walls (48). The plates (36), (38) are made to bias against the walls (48) by springs (44). In the alternative, the chamber walls (48) are made to press against the thermal plates (36), (38). The conformable chamber walls (48) mold to the shape of the heating surfaces to provide maximum thermal contact between surfaces.

Figure 3:
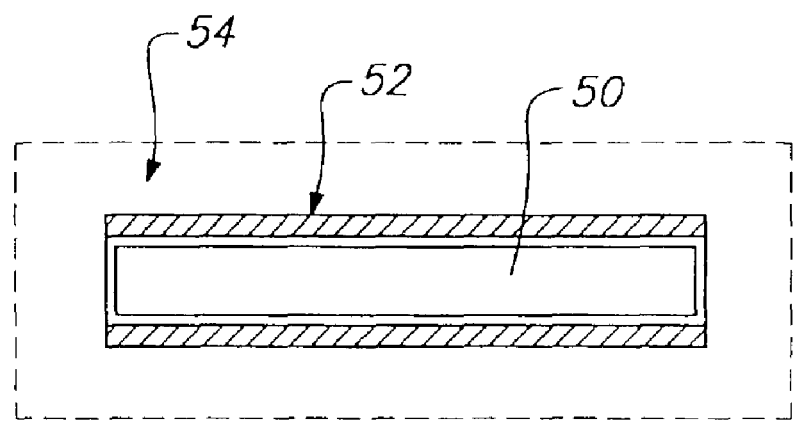
FIG. 3 shows a plan view of a reaction vessel inserted in a thermal sleeve having a heating element and cooling unit according to one embodiment of the present invention.

Further to the ability of the reaction vessel to optimize thermal kinetics, the flexible walls (48) are of low thermal mass to permit rapid heat transfer. FIG. 3 shows a top view of a reaction vessel (50) which is in intimate contact with heating elements (52) and surrounded by cooling chamber (54). The thickness of each flexible wall is preferably between about 0.0001 to 0.020 inch, more preferably 0.0005 to 0.005 inch, and most preferably 0.001 to 0.003 inch. In order to achieve this thinness, the wall may be a film, sheet, or a molded, machined extruded or cast piece, or other convenient thin and flexible structure.

Referring again to FIG. 1, the material composing the flexible walls (18) may be a polyalcohol including polypropylene, polyethylene, polyester, and other polymers, laminates or homogenous polymers, metals or metal laminates, or other materials which may be thin, flexible, conformable and permit high heat transfer and is preferably in the form of a film or sheet. Where the rigid frame (16) of the vessel which supports the walls (18) is a particular material, such as polypropylene, the walls (18) are preferably the same material, such as polypropylene, so that the heat expansion and cooling rates of the walls (18) are the same as the frame (16). Therefore, undue heat or cooling-induced stresses on the materials are minimized so that wrinkling of the walls (18) is avoided during multiple temperature cycling.

Although the flexible walls are preferred, in some embodiments, the walls which contact the heating elements may also be rigid and flat to communicate with a rigid and flat heater. Whether rigid or flexible, the walls which contact the heating elements are typically the major walls of the chamber. The chamber also has a plurality of minor walls provided by the rigid frame which support the major walls.

FIGS. 4a, b, c, d show another embodiment of a reaction vessel (60) with minor walls of the reaction chamber (76) angled to optimize optical viewing. As shown in FIGS. 4a and 4b, five contiguous minor faces or walls (62), (64), (66), (68), (70) couple together two opposing major faces or walls (72), (74) to form the reaction chamber. Minor walls (64), (66) are coupled together at an angle. As shown in FIG. 4c, the angled walls (64), (66) may define the bottom portion of the reaction chamber (76), and back walls (78) may define the top portion of the chamber. A channel (80) leads to the chamber (76). The channel and chamber including the backwalls may optionally be a separate piece inserted into the main body of the reaction vessel. The channel (80) leading to the chamber (76) may serve a variety of functions including providing a conduit for filling the chamber, such as by bottom filling, or providing an area to hold overfilled reagents and purged air.

The angled walls (64), (66) may be joined to form a "V" shaped point (82), especially on the bottom of the chamber (76) to allow for easier filling by reducing or eliminating bubble formation. Alternatively, the interface of the angled walls need not connect to form a point, but may be separated by an intermediary portion, such as another minor wall or various mechanical or fluidic features which do not significantly interfere with the thermal and optical performance of the chamber (76). For example, the angled walls may meet at a port which leads to another processing area in communication with the reaction chamber (76), such as an integrated capillary electrophoresis area.

The reaction vessel also includes a port for adding liquids and removing air from the chamber (76). The port allows access of a pipette tip through the channel (80) into the interior of the chamber (76), for example, to the bottom of the chamber to enable bottom-up filling. The port may also permit other conventional methods of sample introduction, such as through an automated fluid injection system or through a fluidic manifold which optionally is an integral part of the reaction vessel. The vessel may also be one aspect of a larger device which processes the fluid prior to the fluid flowing through the port and into the chamber. One example of a larger device is a disposable fluidic cartridge as disclosed in copending U.S. patent application Ser. No. 08/998,188 filed Dec. 24, 1997, the disclosure of which is incorporated by reference herein.

The external terminus of the port is designed to be sealed, preferably by accepting a seal cap (84), as shown in FIG. 4d. The cap (84) provides a means for sealing the port after filling to provide a barrier between the thermally controlled interior reaction volume and the non-thermally controlled environment to inhibit contamination of the sample, to prevent evaporation of fluid during heating of the sample, and the like. In various embodiments anticipated by the present invention, the seal may be a snap-on cap, a screwtop, or other specialized closure as needed for the selected analytical protocol. Such a cap may be composed of any convenient material such as polypropylene or an elastomer, such as Santoprene™ (trademark of Monsanto Corporation, located in San Louis. Mo.). In one embodiment, the chamber may be further sealed from the exterior environment by the heating of plastic material on or composing the top minor wall. In another embodiment the seal is created by a drop of oil placed on top of an aqueous sample to prevent evaporation of the sample.

Referring again to FIG. 1, the cap (12) may also be a plug which is inserted into the channel (8) in communication with the reaction chamber (10) such that the plug creates an increase in pressure within the chamber (10). The resulting increased pressure causes outward expansion of the flexible walls (18) to force the walls against the external heating units creating a better contact between the walls and the heating elements. The increased pressure may also allow for a solution in the chamber to remain in a liquid state without going into a gaseous state at certain high temperatures. This property is in accordance with the theoretical principle, PV=nRT, where P is pressure, V is volume, n is moles, R is a constant and T is temperature.

The reaction vessel may be configured to optimize the visualization of the reaction in the chamber. To this end one, two or more minor walls of the chamber comprise the optical windows. Where two windows are present, one window may serve as a light excitation entry port and the second window for detection of light emitted from the reaction chamber. In another embodiment, both windows serve for excitation and detection for two light paths. In the first light path, light is radiated through the first window and detected through the second window. In the second light path, light is emitted through second window and detected through the first window. The window faces may be offset at an angle selected to maximize the detection process.

Figure 5:
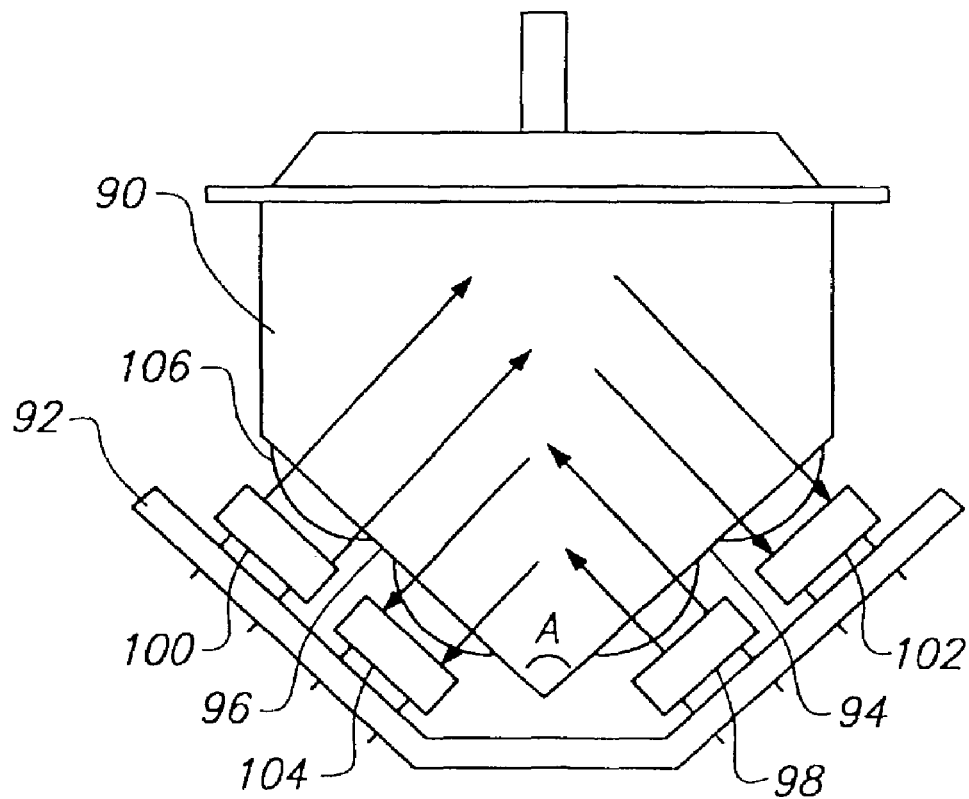
FIG. 5 shows a schematic, side view of a reaction vessel with lenses for optical detection in arrangement with light sources and optical detectors.

FIG. 5 shows a reaction vessel (90) associated with an external optical system (92). Optical system (92) is designed to illuminate the light transmissive, minor wall (94) with optical excitation radiation from individual light source (98) and to detect light emitted from the chamber through the light transmissive, minor wall (96) with detector (104). In the alternative, both adjacent optical walls (94), (96) may receive radiation from respective light sources (98), (100) and observation by detectors (102), (104), where the excitation light which is radiated through each wall is a different wavelength and light detected at each wall is also a different wavelength. Exemplary paths of differing wavelengths of excitation and detection light are shown by arrows in FIG. 5. Each of the walls (94), (96) may additionally have lenses (106) directly molded into its surface to direct the light. Optimum optical sensitivity is attained by maximizing the optical sampling path-length of both the light beams exciting the chemical molecules and the emitted light that is detected to generate the optical signal.

Where excitation and detection occurs at different walls as in FIG. 5, it is usually preferred that the optical walls (94), (96) are offset at an angle (A). The preferred angle is about 90°. A 90° angle between excitation and detection optical paths assures that a minimum amount of excitation radiation entering through one optical wall will exit through the other optical wall. Also the 90° angle permits a maximum amount of emitted radiation, e.g. fluorescence, to be collected through the detection window. In other embodiments, the angle between adjacent optical walls is larger or smaller than 90°, depending, inter alia, on the efficiency and sensitivity of the excitation and detection optics. For example, where a detection system effectively discriminates between excitation and emitted light, an angle of less than 90° between walls may be desired. Conversely, where a detection system fails to efficiently discriminate between excitation and emitted light, an angle greater than 90° may be of interest.

One or more light transmissive elements may be present on the optical walls. The optical elements may be designed, for example, to maximize the total volume of solution which is illuminated by an LED excitation source, to focus an optical excitation source on a specific region of the reaction chamber, or to collect as much fluorescence signal from as large a fraction of the reaction chamber volume as possible. In addition, gratings for selecting specific wavelengths, filters for allowing only certain wavelengths to pass, and multiple lenses or filters optimized for multiple excitation sources or detectors may be used. In another embodiment, the opposite wall may be optimized to collect and focus the maximum percentage of emitted fluorescence signal from the solution to an array of photodetectors. Alternatively, the optical walls may be simple, clear, flat windows serving as optically transmissive windows. Other elements include colored lenses to provide filtering functions, retro-reflective surfaces, optical grating surfaces, etc.

Further to the reaction vessel, the major or minor walls defining the reaction chamber may be adapted for additional optical interrogation. The wall surfaces may be coated or comprise materials such as liquid crystal for augmenting the absorption of certain wavelengths. The surfaces may be used to determine the temperature of the enclosed chemicals by detecting particular absorption bands which reflect temperature conditions.

Thin films of metals, polymers, and combinations of materials such as in laminates, not only can be employed in a reaction chamber for the structural and thermal properties, but for optical properties as well. Thin films constitute materials having a thickness ranging from a few angstroms to hundreds of microns, and are usually formed with a particular series of processes familiar to those in the art of vapor deposition, plasma deposition, magnetron and RF sputtering, laser ablation, etc. For example, vapor-deposited thin films of silver can augment the detection and collection of raman (inelastic scattering of an optically excited source) spectra. This and other materials can be deposited on a variety of substrates (glass, plastic, silicon, metals, etc.) to be translucent (transmitting) in certain wavelengths at angles of incidence, and reflective in others. This is the basis of a lot of optical materials developments and devices such as dichroic beam splitters, dielectric band pass filters, neutral density filters, etc.

The use of these capabilities to manufacture films that can be attached to, used to hermetically seal reaction vessels, or are deposited directly onto the wall of a reaction vessel that will be optically interrogated, can result in reaction vessels with specific optical emission and excitation properties. These thin film processes when used economically, can thereby be used to manufacture reaction vessels inexpensively resulting in disposable vessels with fine-tuned optical properties.

The reaction vessel may be fabricated in various ways. It may be molded in several pieces which are bonded together or injection molded in one piece. There are several advantages to the multi-piece design and manufacturing approach. One benefit is that very thin walls can be achieved where the walls can be consistently produced to be the same size and shape. Another benefit is that the optical features of the device are separated from the fluidic features so that both components can be independently designed and optimized. For example retro-reflective walls may be made on one or many sides of the chamber to reflect light. A third advantage is that the primary optical component can be fabricated from a different material than the primary fluidic component. An additional benefit is that the major surfaces may be fabricated from a different material than some or all of the minor surfaces. For example, materials with optimal thermal characteristics may be different from those with optimal optical characteristics. In particular, the angled optical windows, with or without light components, could be molded from polycarbonate, which has good optical transparency, while the rest of the chamber could be molded from polypropylene, which is inexpensive and is known to be compatible with the sensitive PCR reaction. Both pieces can be bonded together in a secondary step. The optical window is press-fitted or bonded into an end of the chamber, preferably the bottom of the chamber.

In one method of fabricating a reaction vessel, the rigid frame is molded to form a chamber having open sides. The frame is made by standard injection molding processes for thermal materials. After the frame is made, the major walls are produced by placing and preferably stretching material (e.g., thin plastic films or sheets) over the chamber area. The walls are then bonded to the frame. Where the walls are a film or sheet, the material may be attached by heat sealing, adhesive bonding, ultrasonic bonding, etc., to the frame.

A chamber in which the major and minor walls are fabricated from the same material requires that the total surface area of the major surfaces be at least about twice that of the total surface area of the minor surfaces where a thermal conductance ratio of 2:1 is desired. On the other hand, if the walls are made of different materials, it is possible to modify the geometry from that shown since major walls comprised of materials with high thermal conduction could be combined with minor walls of low thermal conduction. The walls may be fabricated from glass or polymers including polyacrylics, polyamides, polycarbonates, polyesters, and vinyl polymers, or any combination thereof.

An insert separate from the main frame of the reaction vessel may be placed inside of the vessel to define some of the chamber or other internal features. The insert may fill the top of the chamber and provide some of the walls. The insert may be bonded or preferably press-fitted into the vessel. The insert may also provide the channel, port, and cap attachment means.

The shape of the chamber may differ according to the particular reaction being performed and the associated thermal transfer device. Furthermore, the relationship of the frame to the flexible walls may vary as long as the frame is coupled to the walls and the walls are accessible to contact an external thermal source. The reaction vessel may be sized, in particular in the chamber, to contain volumes from nanoliters to milliliters, depending upon the desired use. The volume of the chamber is preferably in the range of 1 to 1000 microliters, more preferably in the range of 1 to 500 microliters, and most preferably in the range of 10 to 100 microliters.

In summary of the reaction vessel, the various embodiments have the following characteristics: high surface-to-volume ratio for efficient heating/cooling; thin, low-mass walls; conformable sidewalls to maximize association with heating and cooling system; moldable and bondable material where multiple pieces are required; features which accommodate high thermal expansion coefficients to minimize temperature-induced mechanical stress during heat exchanging operations; chemically inert materials so that there is no adsorption or reaction with reactants, intermediates, or products, no or minimal inactivation of enzymes by surface active means, and compatible with glycerol; windows with high optical clarity for efficient interrogation; long excitation optical path lengths; maximized offset between excitation and emission detection windows; no or minimal light coupling between excitation and detection devices; optical elements such as retro-reflective surfaces; major walls precisely mated with module heating/cooling surfaces; a port for introducing sample and reagents; means to preclude or minimize refluxing during cycling; efficient removal of air during filling and capping; and sealing of the reaction mixture from external environment.

Thermal Sleeve

The reaction vessel is compatible with a thermal sleeve for heating or cooling the mixture in the chamber. The thermal sleeve is designed to induce a temperature change in the chamber by making intimate contact with the walls of the chamber.

Figure 6:
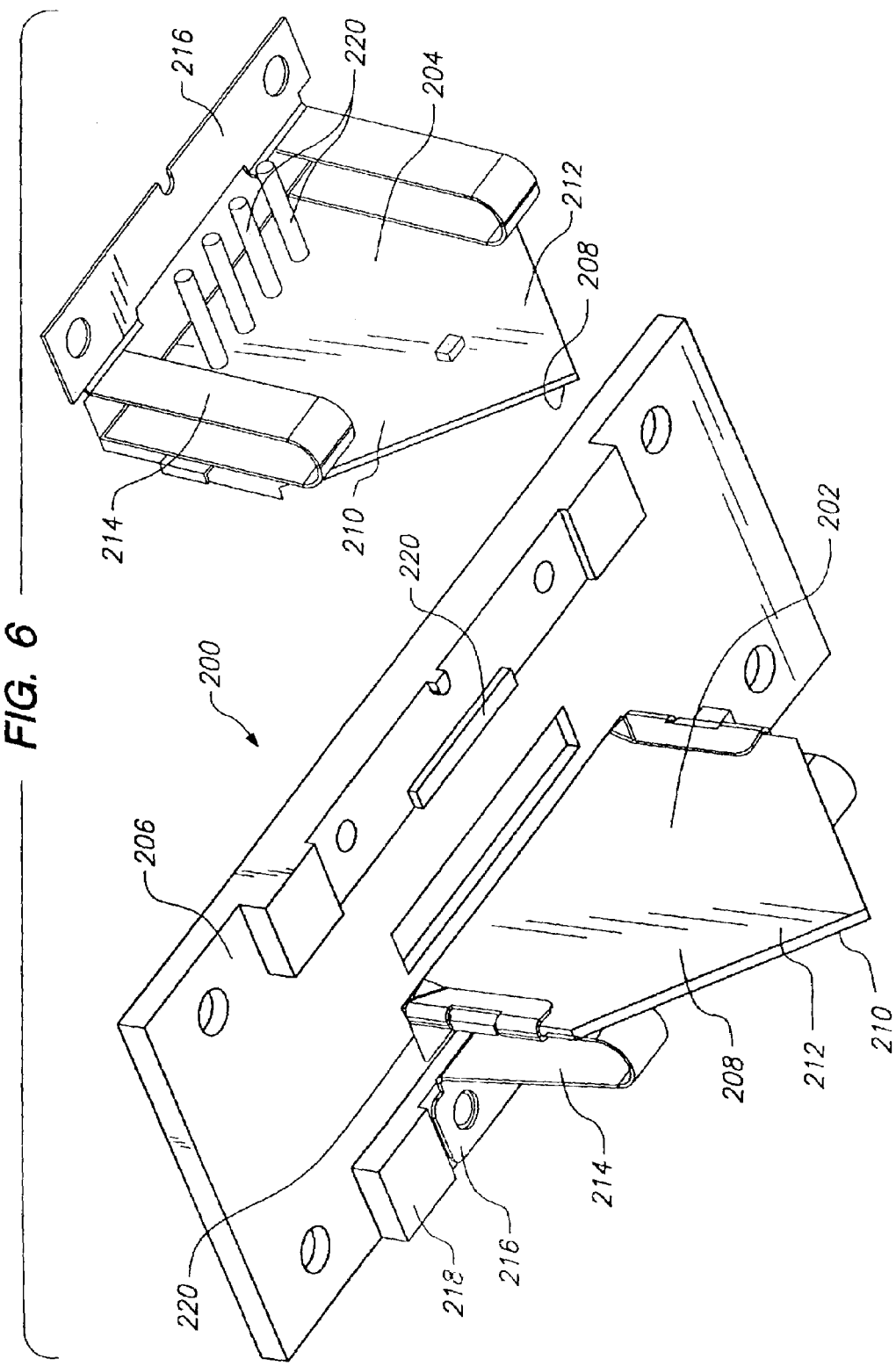
FIG. 6 shows a partially exploded, isometric view of a thermal sleeve with one heating plate attached to a support and, for illustration purposes, the other plate removed from the support.

FIG. 6 shows a partially exploded view of one thermal sleeve (200) with one heating or cooling plate (202) attached to a support bridge (206) and another plate (204) removed from the support (206). Each of the plates (202), (204) has one face being a contact surface (208) and another face being a biasing surface (210) with one end (212) of each plate being slanted towards each other. Each biasing surface (210) may be biased by a spring (214) with an integral attachment arm (216) for coupling to support bridge (206) at securing region (218). The plate is partially inserted through bridge slots (220) and the plate attachment arm (216) is fastened to the bridge securing region (218). The biasing surfaces (210) of the plates also have a plurality of electrical connections (220) which may communicate with heating, cooling or electrical sources (not shown) or any combination thereof. When assembled, the plates are held in opposition by the support bridge to form an opening between the plates for enclosing a reaction chamber.

Figure 7:
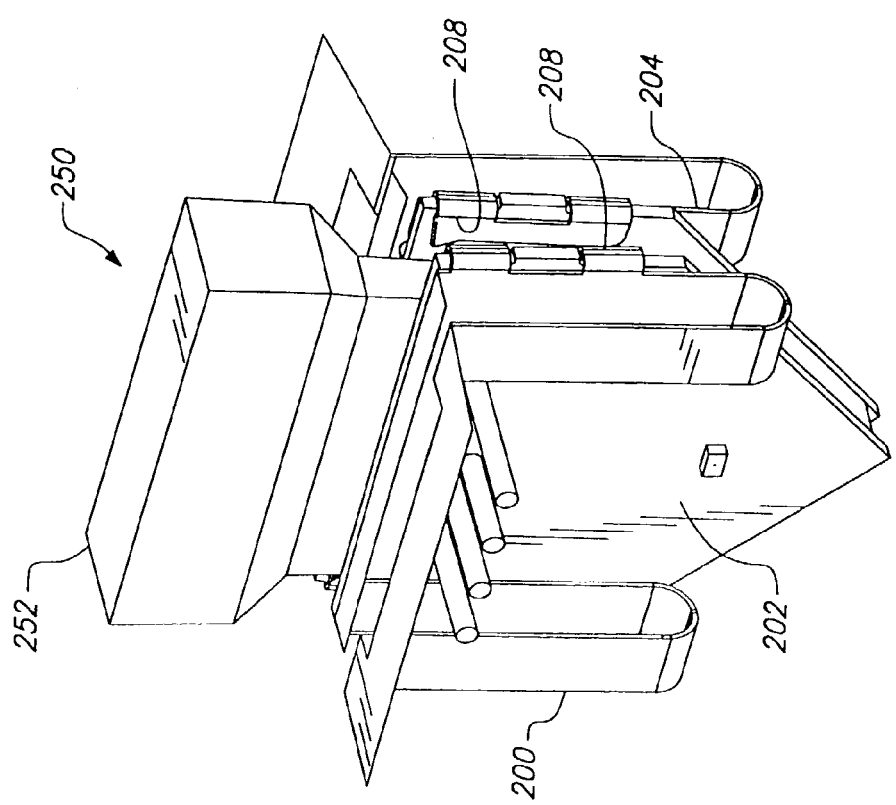
FIG. 7 shows an isometric view of another heat exchanging assembly with a reaction vessel inserted in a thermal sleeve.

FIG. 7 demonstrates how a reaction vessel (252) may be enclosed within the thermal sleeve to form a heat exchanging module (250). The contact surface (208) of each plate (202), (204) is made to press against the reaction chamber surfaces in a manner that maximizes thermal contact. In general, the sleeve may include one or more separate spring-loaded heater plates configured to mechanically bias against the surface, e.g. chamber area, of the reaction vessel. Such a spring-loaded configuration would simplify mechanical tolerances between the various mechanical components, i.e. thermal sleeve, vessel, and optical unit. Alternatively, the plates may be made to bias against a reaction chamber surface by mechanical force initiated by other parts or a mechanical motor, thermal expansion, pneumatic pressure, such as air flow pressure, hydraulic pressure, and the like. The interior of the heat exchanging sleeve may also be tapered to allow for a snug fit with an inserted reaction vessel. Furthermore, the walls of the inserted chamber are expanded to also press against the heater plate surfaces.

The shape of the sleeve is designed for optimal thermal contact with a reaction chamber. In one embodiment, the opening in the sleeve for contacting the chamber walls is elongated in the x-direction. Thus, the opening is longer in the direction perpendicular to the length of the chamber. Preferably the shape of the opening is rectangular in cross section. The ratio of length to width of the surfaces defining the opening may be at least 2:1. Such elongation provides greater contact with the chamber walls than prior designs where the opening for inserting a vessel is expanded in the z-direction and the opening is typically round or octangular in shape to hold round tubes.

As described in this application, the achievement of rapid heat exchange (heating and/or cooling) from a sample in a reaction tube or vessel requires a low thermal-mass thermal sleeve assembly together with a thin, wide reaction vessel. The fastest thermal cycling instruments to date solve this problem by making the reaction vessel a thin long cylinder, 1 mm in diameter or less. Other fast thermal cycling instruments depend on very small liquid sample volumes, which are relatively easy to heat and cool rapidly. However, these approaches are only suitable for very small sample volumes.

In contrast, the reaction vessel described here is thin and wide. Instead of increasing the volume capacity by simply making the reaction vessel longer, this application teaches that large heating and cooling rates can also be achieved by properly designed reaction vessels which are, instead, thin and wide. The counterpart and complementary design of the low-mass thermal sleeve assures that the entire assembly, including the relatively large sample volumes (up to and over 100 µL), can be controllably heated and cooled at the maximum rates.

The thermal plates may be made of various materials. In order to ensure that the inside of the heat exchanging sleeve is resistant to bleach and other cleaning solutions, the interior may be coated or lined with a chemically inert material, such as a polytetrafluoroethylene, or the entire sleeve may be fabricated from a chemically stable material, such as a ceramic or metals such as aluminum nitride, aluminum oxide, beryllium oxide, and silicon nitride. Other materials which may be utilized include, e.g., gallium arsenide, silicon, silicon nitride, silicon dioxide, quartz, glass, diamond, polyacrylics, polyamides, polycarbonates, polyesters, polyimides, vinyl polymers, and halogenated vinyl polymers, such as polytetrafluoroethylenes. Other possible materials include thermocouple materials such as chrome/aluminum, superalloys, zircaloy, aluminum, steel, gold, silver, copper, tungsten, molybdenum, tantalum, brass, sapphire, or any of the numerous ceramics, metals, and synthetic polymeric materials available in the art.

Ceramic plates are preferred because the inside surfaces may be conveniently machined to very high smoothness for high wear resistance, high chemical resistance, and good thermal contact to reaction vessels. Ceramic plates can also be made very thin (between 0.025-0.050 inches) for low thermal mass. A heat exchanging plate made from aluminum or copper also has high thermal conduction, but a larger thermal mass.

The heating source, such as heating resistors, may be directly screen printed onto a plate, particularly plates comprising ceramic insulating materials, such as aluminum nitride and aluminum oxide. Screen printing provides high reliability and low cross-section for efficient transfer of heat into the chamber itself. The heating element may also be baked inside of the ceramic plate. Also, thick or thin film resistors of varying geometric patterns may be disposed on the plate walls to provide more uniform heating, for example by having thicker resistors at the extremities and thinner resistors in the middle. Heating elements may consist of carbide, tungsten, silver, or other materials which heat when a voltage is applied to the material. One way of heating a metal sleeve is by using a laminated heater source such as an etched-foil heating element (Minco Products, located in Minneapolis, Minn.) attached to the surface of the heating plates. Optionally, cooling fins, of the same or different material as the body of the chamber, may be brazed, soldered, or epoxied directly over the screen-printed resistors.

The function of the support bridge (206), shown in the embodiment in FIG. 6 and described above, is to serve as a support for one or more thermal sleeve heating or cooling elements and to provide a guide for inserting the reaction chamber into the thermal sleeve. The support may include a slot for inserting the chamber between the thermal plates. The slot may incorporate mechanical features or a sealing surface which allows a tight mechanical seal. A consideration in the choice of material for the support is that its thermal expansion coefficient (TCE) match that of the thermal plates as closely as possible. The materials of construction recited above for the plate are also useful for the support. Appropriate combinations will be apparent to the skilled artisan.

The mechanical transition between the thermal sleeve plate and top support is a critical joint. The heating or cooling plate may be cycled many times (up to 400,000 over a 5 year life), e.g., in PCR applications between about room temperature, 60° C., and 95° C., while the top support may be maintained at a relatively constant temperature. Thermal gradients and stresses are high in this region. Flexible, chemical-resistant adhesives and gasket materials may be used to ensure bonding. Preferred adhesives are epoxy, but a more robust metal sealing technique can be used if the thermal plate is metal or ceramic. Another criteria for the transition region is that the sealing or bonding material and the method for joining the top support to the thermal plate should be resistant to bleaches and other cleaning solutions. It is expected that up to 1000 exposures to cleaning solutions such as 10% bleach and 1% Tween 20 may occur.

The thermal sleeve of this invention has high thermal conduction and low thermal mass to permit rapid heating and cooling. Further, the thermal sleeve is sufficiently durable for repetitive use (as many as 10,000 reaction chamber insertions). The heating elements are integrated into the sleeve to assure rapid, efficient heating. To maximize cooling efficiency, cooling elements may also be attached to the surface such as cooling fins or thermally conductive elements connected to a secondary cooling source. For example, the sleeve may be thermally connected to a Peltier element or to a heat pipe.

FIGS. 8*a, b, c, d* illustrate exemplary variations of heating and cooling configurations of a thermal sleeve. FIG. 8*a* is a top view which looks directly down into the mouth (262) of the sleeve (260). The sleeve is provided with cooling fins (264) and integrated heaters (266). In this embodiment, the sleeve is provided with a thin interior liner (268). FIG. 8*b* is a front view of the cooling fins (264) shown in FIG. 8*a*. FIG. 8*c* is a front view of another sleeve (270) with heating element (276) and cooling fins (274). A proportional-to-absolute zero (PTAT) temperature sensor is shown at (272). FIG. 8*d* is a side view of the sleeve (270) showing screen printed or laminated heating elements (276) beneath the cooling fins (274).

The temperatures of an inserted reaction chamber and/or thermal plates may be monitored by one or more sensors located on the thermal sleeve. In order to achieve the desired 0.5-1.0° C. temperature accuracy, silicon-based, proportional-to-absolute zero (PTAT) thermal sensors may be used. The output of the sensors is linearly proportional to temperature. High precision PTAT temperature sensors can be very small, e.g. 0.5×0.5×1.0 mm. Alternatively, thermistors, thermocouples and resistance temperature detectors (RTD), especially RTD's made from platinum, copper, nickel and nickel-iron may be used. These sensors are easily affixed to the trailing edge of the heat exchanging reaction chamber.

The thermal sleeve is also adapted for optical interrogation of the contents in situ and may incorporate various features, such as lenses and filters, to facilitate optical visualization. In one embodiment, at least two surfaces of the sleeve are optically transmissive, preferably forming the bottom of the sleeve adjacent to the optical windows of an inserted reaction vessel. An important criteria for the window material is transparency or translucency of the window. The window may also simply be an opening in the sleeve through which the reaction chamber may be viewed. In one embodiment, the sleeve is open at the bottom so that a portion of an inserted chamber may extend below the sleeve for direct optical interrogation. Where the window is a particular material, it is preferred that the window be as close a match as possible between the coefficients of thermal expansion (TCE) of the sleeve and the window. For example, a glass having a TCE closely matches that of a ceramic sleeve may be chosen. A plastic window is more suitable if the thermal sleeve is metal. The window material should also be stable to bleach and other cleaning solutions.

The mechanical transition between window and thermal elements is a critical joint. It is desirable to maintain the optics package at a relatively low temperature, or at least constant temperature, while the thermal sleeve is temperature cycled many times. Thermal gradients and stresses are high in this region. Another criteria for the transition region is that whatever sealing or bonding material and method for joining the optical window to the thermal sleeve is used should be resistant to bleaches and other cleaning solutions. In particular, it is envisioned that the inside of the thermal sleeve will be periodically cleaned by pipetting in dilute bleach solutions, followed by water, followed by an alcohol dry. These solutions will be in direct contact with the joint between the optical window and the thermal sleeve. This transition also significantly effects illumination and light-gathering functions of the device.

Controlled Heat Exchanging Unit

The optics assembly may be fabricated in a unit which is configured to accept a thermal sleeve. The unit may additionally have systems for maintaining the environmental temperatures, such as a cooling system, and various control mechanisms to regulate the operations being performed within the sleeve.

Figure 9:
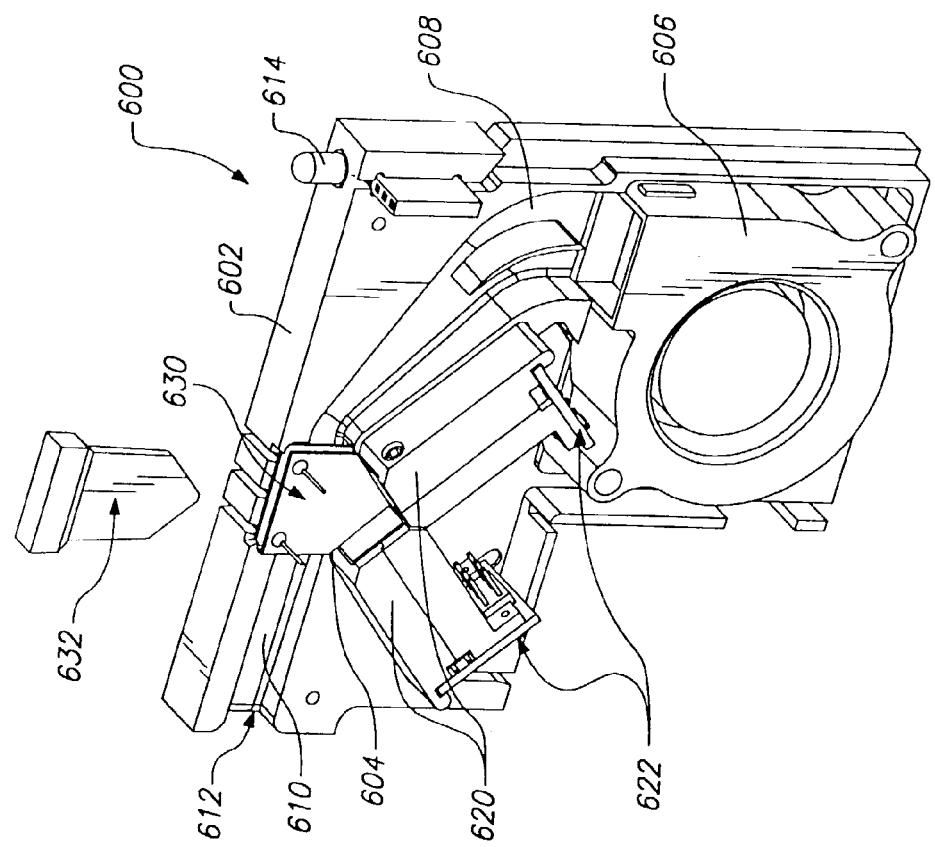
FIG. 9 shows an isometric view of a heat exchanging instrument having a thermal sleeve, optics assembly coupled to circuit boards, and a cooling unit. A reaction vessel is exploded from the instrument.

In FIG. 9, a heat exchanging unit (600) is shown with a housing (602) and associated operational elements. A processing area (604) is adapted to accept a thermal sleeve (630) and reaction vessel (632) described supra. The processing area (604) is in pneumatic communication with a cooling fan (606) by an inlet channel (608) and with an outlet channel (610) leading from the processing area (604) to an outlet port (612). When the vessel (632) is inserted into the sleeve (630), the reaction chamber is cooled by the cooling air circulating from the fan (606) to inlet channel (608), to processing area (604). Thereafter, the air travels through outlet channel (610) to exit the housing at port (612). In addition, the inserted reaction chamber is in optical communication with an optics assembly (620) that includes optics emission and detection blocks coupled to circuit boards (622) for controlling the optics.

The optical assembly (620) includes lensing elements, such as light collimating, e.g. light-pipe, and focussing elements, with transmissive and reflective filters, gratings, photodiodes, fresnel lenses and the like, as needed, which may be attached to a circuit board which may contain LEDs and photodetectors. The lensing components may be injection molded from a transparent plastic such as polycarbonate or other moldable, optically clear plastic or glass. The lensing elements connect the reaction chamber windows to the excitation and detection optical components. The lensing elements incorporate and interface with filters and with the optical excitation and detection circuit boards (622) which contain the solid-state LEDs and photodetectors.

Solid-state LED's and photodetectors are optionally assembled onto a small circuit board located below the lensing components. This is a simple board, fitted with alignment features to accurately position the excitation sources and detectors with respect to the lensing elements and the reaction chamber. An edge-connector or flex-connector provides electrical connection between the optical board and the adjacent controller board.

The housing (602) may be machined from aluminum and anodized, molded from a rigid, high-performance plastic, or other conventional techniques and materials. The primary functions of the housing are to provide a frame for holding the thermal sleeve, top support, and optics assemblies and to provide flow channels and ports for directing cooling fluid, e.g. air, and efficiently guiding the fluid flow across the surface of the thermal sleeve/reaction chamber.

The heat exchanging unit preferably includes a cooling source, such as gas diffusing plates or other air flow distributing structures, for assuring uniform air flow around the thermal sleeve, a fan for blowing cool air over the sleeve, a Peltier device, liquid cooling such as water or a compressed gas cooling source, or the like. The cooling element may be directly formed in the housing or be fabricated independently from the housing and assembled into the housing at a later time. For example, each thermal sleeve in an array of heat exchanging assemblies may communicate with a cooling element. In addition, ports located in the housing may provide coolant air inlet and outlet ports. The ports may also be sealed to a baseplate using suitable sealants, where the ports interface with inlet and outlet ports in the base plate.

FIGS. 10a and 10b show an alternative embodiment of a heat exchanging unit (650). The unit (650) has thermal sleeve (670) (shown partially exploded from the unit) with thermal plates attached to a top support (674) for mating with the housing (652). Housing (652) has air inlet and outlet port (654), a support (656) with air diffusing plates (658) and an optics module (660) with attached circuit board (662). The direction of cooling air flow is shown by the arrows.

The entire electronic control of each heat exchanging unit may be incorporated into one or two circuit boards or chips attached to the sides of the housing. In FIG. 10b, the thermal sleeve (670) with top support (674) is shown partially exploded out of the housing (652). Optics module (660) and optics circuit board (662) interfaces with a pair of controller boards (644). The circuit board (662) and controller boards (644) may be fabricated using high reliability, low-profile surface-mount technology. The controller boards (644) communicate with the optical board through a slot in the housing and a 90° electrical connector where the bottom end of the circuit board plugs into an electrical socket on the base-plate for electrical communication to the controller board.

Moreover, multiple heat exchanging units may be grouped together, as in conventional reaction apparatus, such as PCR, for exposing multiple samples to the same temperature profile, in which case only one unit need be equipped with electrical control circuitry. However, when it is desired to react multiple samples independently, then independent control of each unit or grouping of units is needed.

Figure 11A:
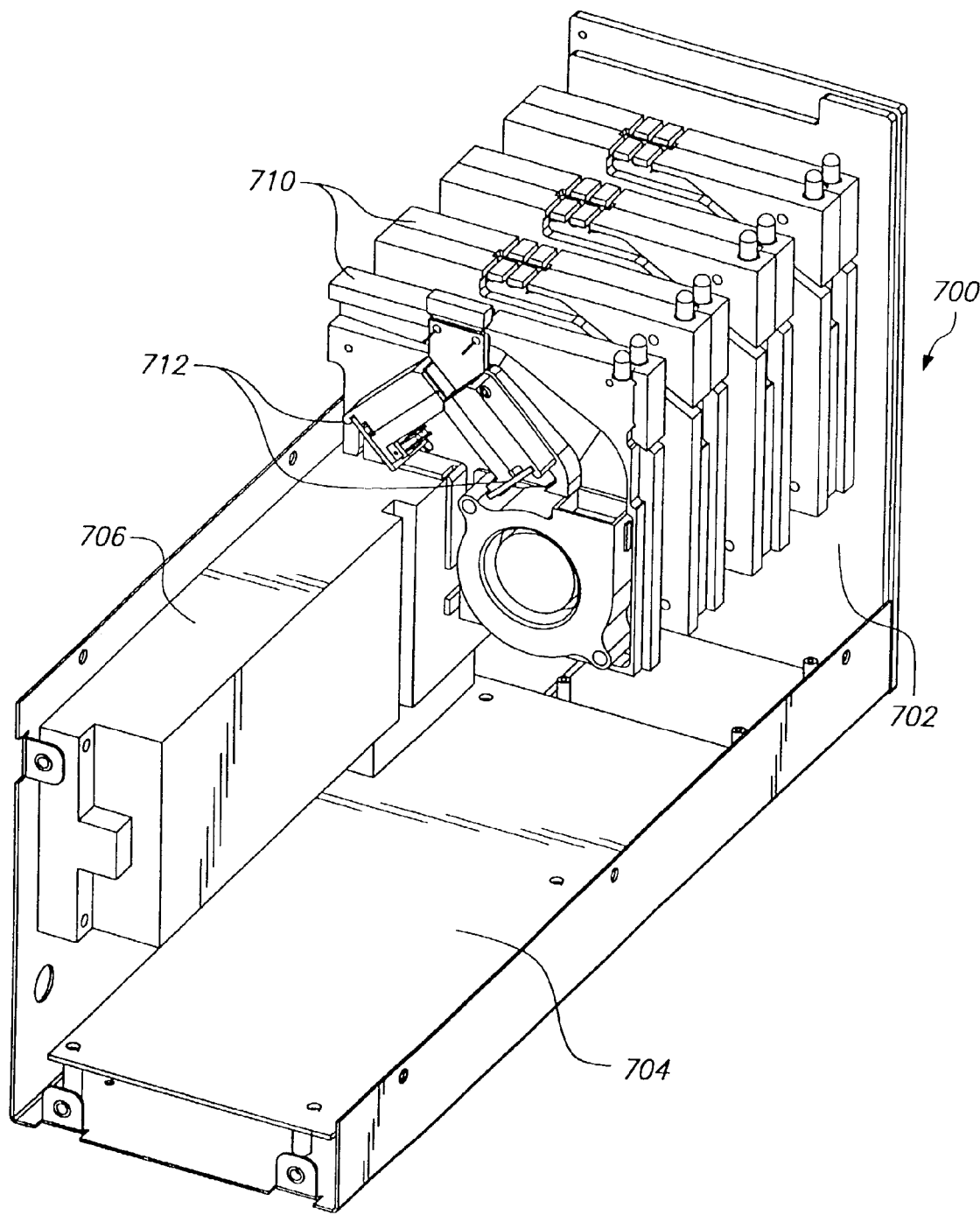
FIGS. 11a, b and c show schematic views of a cluster of modular, heat exchanging units on a base support.
Figure 11B:
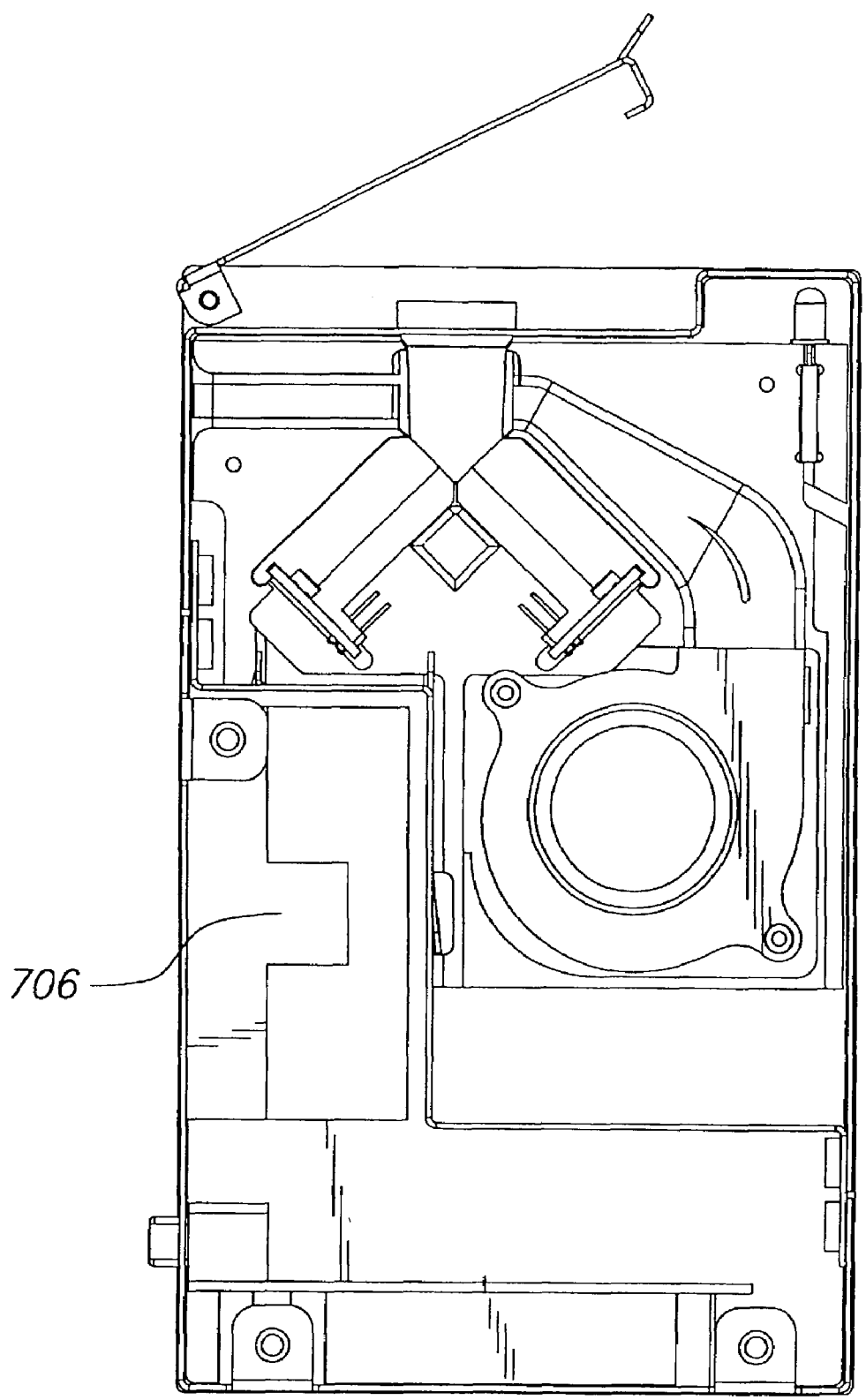
FIG. 11b shows one of the units of FIG. 11a in pneumatic and electrical communication with the base support.

In FIGS. 11a and 11b, a cluster of modular, heat-exchanging units are arranged in an array. FIG. 11a shows one embodiment of a heat exchanging system (700) with four modular units (710), one of which is shown with a side panel removed to expose the internal unit, on a base support (702).

Figure 11C:
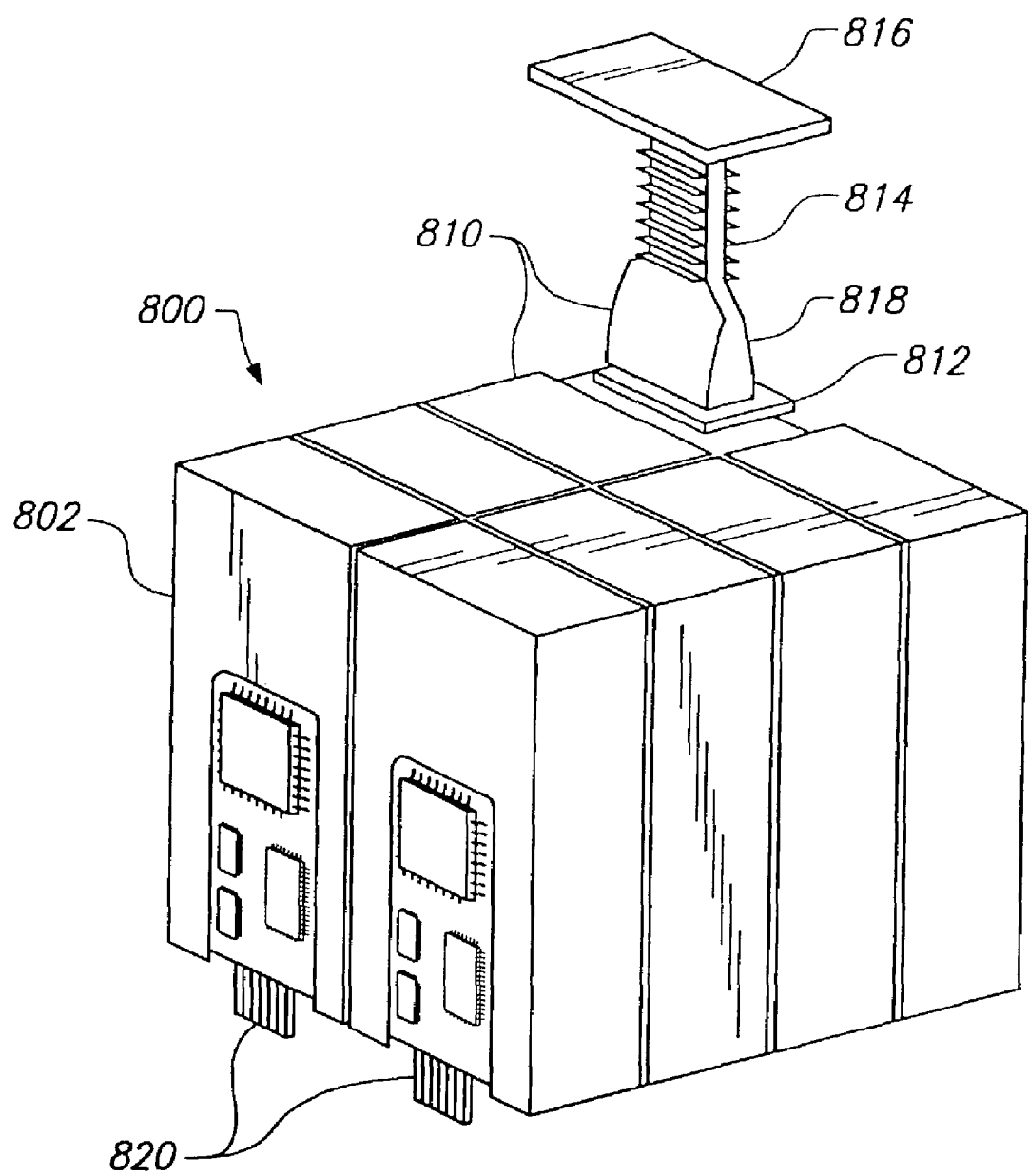
FIG. 11c shows eight units interfacing individual controller boards.

FIG. 11c shows another embodiment of a heat exchanging system (800) with eight modular units (810) arranged on a base support (802). In FIG. 11a and in the cross-sectional view shown in FIG. 11b, each unit (710) has optics circuit boards (712) which interface with the "mother" command unit (704), e.g., a common controller board. The single controller board has several, e.g. four, circuit boards (not shown) so that the "mother" processor board (704) controls the cluster of units (710). A system power converter (706) supplies power to the units (710).

Alternatively, as shown in FIG. 11c, the optics circuit board (812) of each unit (810) interfaces with an individual controller board (820) so that each unit has its own controller board. In FIG. 11c a thermal sleeve (814) with top support (816), optics assembly (818) and optical circuit board (812) are shown removed from the base (802). In an array format, the gap between the heat exchanging units may be sealed by a gasketed plate covering the entire array. The top support and the gasketed plate may be configured to form a flush surface for a multi-unit array. The gasket material is preferably resistant to bleach and other cleaning solutions.

Referring again to FIG. 11a, the base support (702) for the array of modular units (710) may provide several functions. For example, the base may allow for physical mounting of the units, housing of a controller board (704), and electrical connection between the units and a host computer. A multi-function electrical connector may also serve as the physical mount.

The footprint of the controlled heat exchanging unit is designed to be easily assembled into 2-dimensional arrays. In addition, the close spacing in one direction allows the use of linked linear arrays of units, if desired. In one embodiment, the overall dimensions of each modular unit are approximately 9×40×50 mm. The narrow dimension is small enough to allow, for example, 8 units to be grouped together, if desired, in a reasonable (72 mm) length, suitable for interfacing with standard commercially available multi-pipettes which have 9 mm center-to-center spacing for convenient loading of sample and chemicals, if needed.

The thermal reaction apparatus may find use in many applications. The apparatus of the invention may be utilized to perform chemical reactions on a sample, for example, polymerase chain reaction (PCR). Each unit is provided, either directly or within a separate, insertable reaction vessel, with reagents required for the reaction. For example, in performing a polymerase chain reaction, the chamber of the vessel may include a sample polynucleotide, a polymerase such as Taq polymerase, nucleoside triphosphates, a first primer hybridizable with the sample polynucleotide, and a second primer hybridizable with a sequence complementary to the polynucleotide. Some or all of the required reagents may be present in the reaction chamber as shipped, or they may be added to the sample and then delivered through the inlet port to the chamber, or the reagents may be delivered to the chamber independently of the sample. The polymerase chain reaction may be performed according to methods well known in the art.

Although polynucleotide amplification by polymerase chain reaction has been described herein, it will be appreciated by persons skilled in the art that the devices and methods of the present invention may be utilized equally effectively for a variety of other polynucleotide amplification reactions and ligand-binding assays. Such additional reactions may be thermally cycled, such as the polymerase chain reaction, or they may be carried out at a single temperature, e.g., nucleic acid sequenced-based amplification (NASBA). Moreover, such reactions may employ a wide variety of amplification reagents and enzymes, including DNA ligase, T7 RNA polymerase and/or reverse transcriptase, among others. Additionally, denaturation of polynucleotides can be accomplished by known chemical or physical methods, alone or combined with thermal change. Polynucleotide amplification reactions that may be practiced in the apparatus of the invention include, but are not limited to: (1) target polynucleotide amplification methods such as self-sustained sequence replication (3SR) and strand-displacement amplification (SDA): (2) methods based on amplification of a signal attached to the target polynucleotide, such as "branched chain" DNA amplification; (3) methods based on amplification of probe DNA, such as ligase chain reaction (LCR) and QB replicase amplification (QBR); (4) transcription-based methods, such as ligation activated transcription (LAT) and nucleic acid sequence-based amplification (NASBA); and (5) various other amplification methods, such as repair chain reaction (RCR) and cycling probe reaction (CPR).

In addition to the aforementioned gene or target amplification methods, other chemical or biochemical reaction applications are anticipated. For example, temperature controlled lysis of cells is another application of the intended invention, which may or may not compliment gene or target amplification methods described above. In many cases, this is accomplished by raising the temperature of the solution containing the cell to 37° C. for a few minutes to allow the action of proteolytic enzymes followed by raising the temperature and holding at 95° C. After a few seconds to minutes, the cell is lysed and the target component, such as nucleic acid, is released and can then be further processed, e.g., amplified. In other applications, it may be desired to immediately stop any further chemical reactions immediately after the lysis by lowering the temperature to 0° to 4° C., such as in the case when studying the mRNA expression state using rapid thermal polymerase chain reaction. The rapid thermal ramping as provided by this apparatus enables such functionality.

Furthermore, the disclosed apparatus can be utilized to control and interrogate chemical reactions. In enzyme kinetic studies, for example, it is advantageous to hold the test reaction mixture at a reduced temperature, such as 0° C.-4° C., before starting the reaction, and then to quickly bring the reaction mixture from this reduced hold temperature, e.g. 4° C., to an optimal reaction temperature. Unwanted side reactions occurring at intermediate temperatures are reduced or eliminated, allowing for more accurate measurements and higher purity of product. Moreover, this approach can be extended to more complex chemical and biochemical reactions that can be controlled and studied by enabling changes to multiple different temperatures, or to periodically reduce the temperature to stop the reactions.

Such temperature control can be exploited for ligand binding reactions such as fluorescence homogenous immunoassays. Because the reaction start event can be precisely executed and the subsequent reaction hold temperature accurately controlled without thermal gradients, better assay performance may be achieved. Other applications of the invention are intended to be within the scope of the invention where those applications require the transfer of thermal energy to a chemical reaction.

The present invention has been described above in varied detail by reference to particular embodiments and figures. However, it is to be understood that modifications or substitutions may be made to the devices and methods described based upon this disclosure without departing from the broad scope of the invention. Therefore, the scope of the invention should be determined by the following claims and their legal equivalents.

What is claimed is:

1. An apparatus for controlling the temperature of a sample, the apparatus comprising:
   a) a vessel having:
      i) a reaction chamber for holding the sample, the chamber being defined by two opposing major walls and a plurality of rigid minor walls joining the major walls to each other, wherein at least one of the major walls comprises a sheet or film;
      ii) a port for introducing fluid into the chamber; and
      iii) a channel connecting the port to the chamber;
   b) at least one heating surface for contacting the sheet or film; and
   c) a plug that is insertable into the channel to increase pressure in the chamber, whereby the pressure increase in the chamber forces the sheet or film against the heating surface.

2. The apparatus of claim 1, wherein at least two of the walls are light transmissive, and wherein the apparatus further comprises optics for optically interrogating the chamber while the heating surface is in contact with the sheet or film, the optics comprising at least one light source for transmitting light to the chamber through a first one of the light transmissive walls and at least one detector for detecting light exiting the chamber through a second one of the light transmissive walls.

3. The apparatus of claim 2, wherein the at least one heating surface is provided by a thermal sleeve for receiving the vessel, the sleeve including at least one heater for heating the surface, the sleeve having at least one window or opening providing optical access to the light transmissive walls, and the optics being positioned to interrogate the chamber through the at least one window or opening in the sleeve.

4. The apparatus of claim 1, wherein the heating surface comprises a surface of a plate, the plate having at least one heating resistor coupled thereto.

5. The apparatus of claim 1, wherein each of the major walls comprises a sheet or film, the apparatus includes at least two heating surfaces defined by opposing plates positioned to receive the vessel between them such that the plates contact the major walls, and the apparatus includes means for heating the plates.

6. The apparatus of claim 5, further comprising at least one support for holding the plates in an opposing relationship to each other, the support including a slot for inserting the chamber of the vessel between the plates.

7. The apparatus of claim 5, wherein at least two of the minor walls are light transmissive to provide optical windows to the chamber, and wherein the apparatus further comprises optics for optically interrogating the chamber through at least one window or opening between the plates, the optics comprising at least one light source for transmitting light to the chamber through a first one of the light transmissive walls and at least one detector for detecting light exiting the chamber through a second one of the light transmissive walls.

8. The apparatus of claim 7, wherein the optics include:
   i) a plurality of light sources and filters for transmitting different wavelengths of excitation light to the chamber; and
   ii) a plurality of detectors and filters for detecting different wavelengths of light emitted from the chamber.

9. The apparatus of claim 7, wherein the plates, heating means, and optics are incorporated into a heat-exchanging unit, the apparatus further comprises a base support for receiving the heat-exchanging unit, and the base support includes at least one controller for controlling the operation of the heat-exchanging unit.

10. The apparatus of claim 9, wherein the heat-exchanging unit further comprises:
    i) a housing for holding the plates, heating means, and optics; and
    ii) a cooling element disposed within the housing for cooling the chamber.

11. The apparatus of claim 10, wherein the cooling element comprises a fan for blowing cooling air.

12. The apparatus of claim 11, wherein the base support is constructed to receive and independently control a plurality of such heat-exchanging units.

13. The apparatus of claim 2, wherein the light transmissive walls are angularly offset about 90° from each other, and wherein the optics provide about a 90° angle between optical excitation and detection paths.

14. The apparatus of claim 1, wherein the apparatus includes a heat source for heating the surface, and the apparatus further includes a cooling element for cooling the chamber.

15. The apparatus of claim 14, wherein the cooling element comprises a fan for blowing cooling air.

16. A vessel having a reaction chamber for holding a sample, the vessel comprising:
    a) a rigid frame defining minor walls of the chamber, wherein at least two of the minor walls are light transmissive to provide optical windows to the chamber;
    b) two opposing major walls of the chamber connected to each other by the minor walls; wherein at least one of the major walls comprises a sheet or film; and
    c) a port for introducing the sample into the chamber.

17. The vessel of claim 16, wherein each of the two opposing major walls of the chamber comprises a sheet or film, each of the sheets or films being sufficiently flexible to conform to a respective heating surface.

18. The vessel of claim 17, wherein each of the sheets or films comprise a polymeric material.

19. The vessel of claim 16, wherein the light transmissive walls are angularly offset from each other.

20. The vessel of claim 16, wherein the light transmissive walls are angularly offset from each other by about 90°.

21. The vessel of claim 16, further comprising optical elements or coatings on the light transmissive walls for allowing only certain wavelengths of light to pass through the walls.

22. The vessel of claim 16, wherein each of the light transmissive walls has a lens molded into its surface.

23. The vessel of claim 16, wherein the chamber has at least four minor walls, at least two of the minor walls being the light transmissive walls, and at least two other of the minor walls being retro-reflective walls for reflecting light in the chamber.

24. The vessel of claim 16, further comprising at least one reagent in the chamber.

25. The vessel of claim 16, further comprising sealing means for sealing the port.

26. The vessel of claim 16, wherein the vessel further includes:
    a channel connecting the port to the chamber; and
    a plug that is insertable into the channel to increase pressure in the chamber.

27. The vessel of claim 16, wherein the at least one sheet or film is sufficiently flexible to conform to a heating or cooling surface.

28. The vessel of claim 17, wherein the ratio of the thermal conductance of the major walls to that of the minor walls is at least 2:1.

29. A reaction vessel having a reaction chamber for holding a sample, the vessel comprising:
   a) a rigid frame defining minor walls of the chamber;
   b) two opposing major walls of the chamber connected to each other by the minor walls; wherein at least one of the major walls comprises a sheet or film;
   c) a port for introducing the sample into the vessel;
   d) a channel connecting the port to the chamber; and
   e) a plug that is insertable into the channel to increase pressure in the chamber.

30. The vessel of claim 29, wherein the vessel includes two sheets or films that are attached to opposite sides of the rigid frame to form the two opposing major walls of the chamber, and each of the sheets or films being sufficiently flexible to conform to a respective heating surface.

31. The vessel of claim 30, wherein each of the sheets or films comprise a polymeric material.

32. The vessel of claim 29, wherein at least two of the minor walls are light transmissive to provide optical windows to the chamber.

33. The vessel of claim 32, wherein the light transmissive walls are angularly offset from each other.

34. The vessel of claim 32, wherein the light transmissive walls are angularly offset from each other by about 90°.

35. The vessel of claim 32, further comprising optical elements or coatings on the light transmissive walls for allowing only certain wavelengths of light to pass through the walls.

36. The vessel of claim 29, wherein the chamber has at least four minor walls, at least two of the minor walls being light transmissive to provide optical windows to the chamber, and at least two other of the minor walls being retro-reflective walls for reflecting light in the chamber.

37. The vessel of claim 29, wherein the at least one sheet or film is sufficiently flexible to conform to a heating or cooling surface.

38. The vessel of claim 29, further comprising at least one reagent in the chamber.

39. The vessel of claim 30, wherein the ratio of the thermal conductance of the major walls to that of the minor walls is at least 2:1.

40. The vessel of claim 30, wherein the ratio of the total surface area of the major walls to that of the minor walls is at least 2:1.

41. A reaction vessel comprising:
   a) two opposing major walls, wherein at least one of the major walls comprises a sheet or film;
   b) a plurality of rigid minor walls joining the major walls to each other to form a reaction chamber, at least two of the minor walls being light transmissive; and
   c) a port for introducing fluid into the chamber; wherein the ratio of the total surface area of the major walls to that of the minor walls is at least 2:1.

42. The vessel of claim 41, wherein the sheet or film is sufficiently flexible to conform to a heating or cooling surface.

43. The vessel of claim 41, further comprising sealing means for sealing the port.

44. The vessel of claim 41, wherein the vessel includes a channel connecting the port to the chamber, and the vessel further comprises a plug that is insertable into the channel to increase pressure in the chamber.

45. The vessel of claim 41, wherein the vessel includes a rigid frame providing the minor walls of the chamber, and wherein the two opposing major walls comprise two sheets or films that are attached to opposite sides of the rigid frame.

46. The vessel of claim 45, wherein each of the sheets or films comprise a polymeric material.

47. The vessel of claim 41, wherein the light transmissive walls are angularly offset from each other.

48. The vessel of claim 47, wherein the light transmissive walls are offset from each other by about 90°.

49. The vessel of claim 41, further comprising optical elements or coatings on the light transmissive walls for allowing only certain wavelengths of light to pass through the light transmissive walls.

50. The vessel of claim 41, wherein the vessel includes at least four minor walls defining the chamber, at least two of the minor walls being the light transmissive walls, and at least two other of the minor walls being retro-reflective walls for reflecting light in the chamber.

51. The vessel of claim 41, further comprising at least one reagent in the chamber.

52. A reaction vessel comprising:
   a) two opposing major walls, wherein at least one of the major walls comprises a sheet or film;
   b) a plurality of rigid minor walls joining the major walls to each other to form a reaction chamber, at least two of the minor walls being light transmissive to provide optical windows to the chamber; and
   c) a port for introducing fluid into the chamber; wherein the ratio of the thermal conductance of the major walls to that of the minor walls is at least 2:1.

53. The vessel of claim 52, wherein the sheet or film is sufficiently flexible to conform to a heating or cooling surface.

54. The vessel of claim 52, wherein the vessel includes a channel connecting the port to the chamber, and the vessel further comprises a plug that is insertable into the channel to increase pressure in the chamber.

55. The vessel of claim 52, wherein the vessel includes a rigid frame providing the minor walls of the chamber, and wherein the two opposing major walls comprise two sheets or films that are attached to opposite sides of the rigid frame, each of the sheets or films being sufficiently flexible to conform to a respective heating surface.

56. The vessel of claim 55, wherein each of the sheets or films comprise a polymeric material.

57. The vessel of claim 52, wherein the light transmissive walls are angularly offset from each other.

58. The vessel of claim 57, wherein the light transmissive walls are offset from each other by about 90°.

59. The vessel of claim 52, further comprising optical elements or coatings on the light transmissive walls for allowing only certain wavelengths of light to pass through the walls.

60. The vessel of claim 52, wherein the vessel includes at least four minor walls defining the chamber, at least two of the minor walls being the light transmissive walls, and at least two other of the minor walls being retro-reflective walls for reflecting light in the chamber.

61. The vessel of claim 52, further comprising sealing means for sealing the port.

62. The vessel of claim 52, further comprising at least one reagent in the chamber.

63. A reaction vessel comprising:
a) two opposing major walls, wherein at least one of the major walls comprises a sheet or film;
b) a plurality of rigid minor walls joining the major walls to each other to form a reaction chamber
c) a port for introducing fluid into the vessel;
d) a channel connecting the port to the reaction chamber; and
e) a plug that is insertable into the channel to increase pressure in the reaction chamber.

64. The vessel of claim 63, wherein each of the major walls comprises a sheet or film, and wherein each of the sheets or films is sufficiently flexible to conform to a respective heating surface.

65. The vessel of claim 64, wherein each of the sheets or films comprise a polymeric material.

66. The vessel of claim 63, wherein at least two of the minor walls are light transmissive to provide optical windows to the chamber.

67. The vessel of claim 66, wherein the light transmissive walls are angularly offset from each other.

68. The vessel of claim 66, wherein the light transmissive walls are angularly offset from each other by about 90°.

69. The vessel of claim 66, further comprising optical elements or coatings on the light transmissive walls for allowing only certain wavelengths of light to pass through the walls.

70. The vessel of claim 63, wherein the chamber has at least four minor walls, at least two of the minor walls being light transmissive to provide optical windows to the chamber, and at least two other of the minor walls being retro-reflective walls for reflecting light in the chamber.

71. The vessel of claim 63, wherein the at least one sheet or film is sufficiently flexible to conform to a heating or cooling surface.

72. The vessel of claim 63, further comprising at least one reagent in the chamber.

73. The vessel of claim 63, wherein the ratio of the thermal conductance of the major walls to that of the minor walls is at least 2:1.

74. The vessel of claim 63, wherein the ratio of the total surface area of the major walls to that of the minor walls is at least 2:1.

* * * * *